United States Patent
Jury et al.

(10) Patent No.: US 8,779,245 B2
(45) Date of Patent: Jul. 15, 2014

(54) SOYBEAN VARIETY A1026138

(75) Inventors: Thomas Jury, Madison, WI (US); Charlotte Sartell, Whitewater, WI (US)

(73) Assignee: Monsanto Technology LLC, St. Louis, MO (US)

( * ) Notice: Subject to any disclaimer, the term of this patent is extended or adjusted under 35 U.S.C. 154(b) by 192 days.

(21) Appl. No.: 13/442,805

(22) Filed: Apr. 9, 2012

(65) Prior Publication Data
US 2013/0036489 A1  Feb. 7, 2013

Related U.S. Application Data

(60) Provisional application No. 61/515,291, filed on Aug. 4, 2011.

(51) Int. Cl.
*A01H 1/00* (2006.01)
*A01H 1/02* (2006.01)
*A01H 5/00* (2006.01)
*A01H 5/10* (2006.01)
*C12N 5/04* (2006.01)

(52) U.S. Cl.
USPC ........ 800/312; 800/260; 800/279; 800/300.1; 800/301; 800/302; 800/303; 435/415; 435/426; 435/430.1

(58) Field of Classification Search
USPC ......... 800/260, 312, 279, 295, 301, 302, 303; 435/415, 430.1, 430, 426
See application file for complete search history.

(56) References Cited

U.S. PATENT DOCUMENTS

| | | | |
|---|---|---|---|
| 5,569,815 A | 10/1996 | Eby | |
| 5,576,474 A | 11/1996 | Lussenden | |
| 6,953,876 B2 | 10/2005 | Floyd | |
| 6,958,436 B2 | 10/2005 | Hawbaker | |
| 6,960,707 B2 | 11/2005 | Eby et al. | |
| 6,967,263 B2 | 11/2005 | Narvel | |
| 6,969,787 B2 | 11/2005 | Eby | |
| 6,972,353 B2 | 12/2005 | Eby | |
| 6,972,354 B2 | 12/2005 | Eby | |
| 6,972,355 B2 | 12/2005 | Eby | |
| 6,979,760 B2 | 12/2005 | Eby et al. | |
| 6,982,367 B2 | 1/2006 | Eby | |
| 7,491,870 B2 * | 2/2009 | Eby | 800/312 |
| 7,632,985 B2 | 12/2009 | Malven et al. | |
| 8,053,184 B2 | 11/2011 | Malven et al. | |

OTHER PUBLICATIONS

Allard, In: Principles of Plant Breeding, Chapter 6 through Chapter 9, University of California, Davis, California, John Wiley & Sons, New York, pp. 50-98, 1960.
Eshed et al., "Less-than-additive epistatic interactions of quantitative trait loci in tomato," *Genetics*, 143:1807-1817, 1996.
Fehr, "Breeding methods for cultivar development," In: Soybeans: Improvement, Production and Uses, $2^{nd}$ Edition, Wilcox et al., (Eds.), Madison, Wisconsin, 16, pp. 249 and 259, 1987.
Fehr, Iowa State University, "Principles of Cultivar Development," vol. 1 Theory and Technique and vol. 2 Crop Species, Soybean, Macmillian Publishing Company, New York, pp. 360-376, 1987.
Kraft et al., "Linkage disequilibrium and fingerprinting in sugar beet," *Theor. Appl. Genet*, 101:323-326, 2000.
Sep. 26, 2012 Information Disclosure Statement for U.S. Appl. No. 13/442,805.

* cited by examiner

*Primary Examiner* — Medina A Ibrahim
(74) *Attorney, Agent, or Firm* — Dentons US LLP

(57) ABSTRACT

The invention relates to the soybean variety designated A1026138. Provided by the invention are the seeds, plants and derivatives of the soybean variety A1026138. Also provided by the invention are tissue cultures of the soybean variety A1026138 and the plants regenerated therefrom. Still further provided by the invention are methods for producing soybean plants by crossing the soybean variety A1026138 with itself or another soybean variety and plants produced by such methods.

22 Claims, No Drawings

SOYBEAN VARIETY A1026138

This application claims the priority of U.S. Provisional Appl. Ser. No. 61/515,291, filed Aug. 4, 2011, the entire disclosure of which is incorporated herein by reference.

BACKGROUND OF THE INVENTION

1. Field of the Invention

The present invention relates generally to the field of soybean breeding. In particular, the invention relates to the novel soybean variety A1026138.

2. Description of Related Art

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, better agronomic quality, resistance to herbicides, and improvements in compositional traits.

Soybean, *Glycine max* (L.), is a valuable field crop. Thus, a continuing goal of plant breeders is to develop stable, high yielding soybean varieties that are agronomically sound. The reasons for this goal are to maximize the amount of grain produced on the land used and to supply food for both animals and humans. To accomplish this goal, the soybean breeder must select and develop soybean plants that have the traits that result in superior varieties.

SUMMARY OF THE INVENTION

One aspect of the present invention relates to seed of the soybean variety A1026138. The invention also relates to plants produced by growing the seed of the soybean variety A1026138, as well as the derivatives of such plants. Further provided are plant parts, including cells, plant protoplasts, plant cells of a tissue culture from which soybean plants can be regenerated, plant calli, plant clumps, and plant cells that are intact in plants or parts of plants, such as pollen, flowers, seeds, pods, leaves, stems, and the like.

In a further aspect, the invention provides a composition comprising a seed of soybean variety A1026138 comprised in plant seed growth media. In certain embodiments, the plant seed growth media is a soil or synthetic cultivation medium. In specific embodiments, the growth medium may be comprised in a container or may, for example, be soil in a field. Plant seed growth media are well known to those of skill in the art and include, but are in no way limited to, soil or synthetic cultivation medium. Advantageously, plant seed growth media can provide adequate physical support for seeds and can retain moisture and/or nutritional components. Examples of characteristics for soils that may be desirable in certain embodiments can be found, for instance, in U.S. Pat. Nos. 3,932,166 and 4,707,176. Synthetic plant cultivation media are also well known in the art and may, in certain embodiments, comprise polymers or hydrogels. Examples of such compositions are described, for example, in U.S. Pat. No. 4,241,537.

Another aspect of the invention relates to a tissue culture of regenerable cells of the soybean variety A1026138, as well as plants regenerated therefrom, wherein the regenerated soybean plant is capable of expressing all the physiological and morphological characteristics of a plant grown from the soybean seed designated A1026138.

Yet another aspect of the current invention is a soybean plant comprising a single locus conversion of the soybean variety A1026138, wherein the soybean plant is otherwise capable of expressing all the physiological and morphological characteristics of the soybean variety A1026138. In particular embodiments of the invention, the single locus conversion may comprise a transgenic gene which has been introduced by genetic transformation into the soybean variety A1026138 or a progenitor thereof. In still other embodiments of the invention, the single locus conversion may comprise a dominant or recessive allele. The locus conversion may confer potentially any trait upon the single locus converted plant, including herbicide resistance, insect resistance, resistance to bacterial, fungal, or viral disease, male fertility or sterility, and improved nutritional quality.

Still yet another aspect of the invention relates to a first generation ($F_1$) hybrid soybean seed produced by crossing a plant of the soybean variety A1026138 to a second soybean plant. Also included in the invention are the $F_1$ hybrid soybean plants grown from the hybrid seed produced by crossing the soybean variety A1026138 to a second soybean plant. Still further included in the invention are the seeds of an $F_1$ hybrid plant produced with the soybean variety A1026138 as one parent, the second generation ($F_2$) hybrid soybean plant grown from the seed of the $F_1$ hybrid plant, and the seeds of the $F_2$ hybrid plant.

Still yet another aspect of the invention is a method of producing soybean seeds comprising crossing a plant of the soybean variety A1026138 to any second soybean plant, including itself or another plant of the variety A1026138. In particular embodiments of the invention, the method of crossing comprises the steps of a) planting seeds of the soybean variety A1026138; b) cultivating soybean plants resulting from said seeds until said plants bear flowers; c) allowing fertilization of the flowers of said plants; and d) harvesting seeds produced from said plants.

Still yet another aspect of the invention is a method of producing hybrid soybean seeds comprising crossing the soybean variety A1026138 to a second, distinct soybean plant which is nonisogenic to the soybean variety A1026138. In particular embodiments of the invention, the crossing comprises the steps of a) planting seeds of soybean variety A1026138 and a second, distinct soybean plant, b) cultivating the soybean plants grown from the seeds until the plants bear flowers; c) cross pollinating a flower on one of the two plants with the pollen of the other plant, and d) harvesting the seeds resulting from the cross pollinating.

Still yet another aspect of the invention is a method for developing a soybean plant in a soybean breeding program comprising: obtaining a soybean plant, or its parts, of the variety A1026138; and b) employing said plant or parts as a source of breeding material using plant breeding techniques. In the method, the plant breeding techniques may be selected from the group consisting of recurrent selection, mass selection, bulk selection, backcrossing, pedigree breeding, genetic marker-assisted selection and genetic transformation. In certain embodiments of the invention, the soybean plant of variety A1026138 is used as the male or female parent.

Still yet another aspect of the invention is a method of producing a soybean plant derived from the soybean variety A1026138, the method comprising the steps of: (a) preparing a progeny plant derived from soybean variety A1026138 by crossing a plant of the soybean variety A1026138 with a second soybean plant; and (b) crossing the progeny plant with itself or a second plant to produce a progeny plant of a subsequent generation which is derived from a plant of the soybean variety A1026138. In one embodiment of the invention, the method further comprises: (c) crossing the progeny plant of a subsequent generation with itself or a second plant; and (d) repeating steps (b) and (c) for, in some embodiments, at least 2, 3, 4 or more additional generations to produce an inbred soybean plant derived from the soybean variety A1026138. Also provided by the invention is a plant produced by this and the other methods of the invention.

In another embodiment of the invention, the method of producing a soybean plant derived from the soybean variety A1026138 further comprises: (a) crossing the soybean variety A1026138-derived soybean plant with itself or another soybean plant to yield additional soybean variety A1026138-derived progeny soybean seed; (b) growing the progeny soybean seed of step (a) under plant growth conditions to yield additional soybean variety A1026138-derived soybean plants; and (c) repeating the crossing and growing steps of (a) and (b) to generate further soybean variety A1026138-derived soybean plants. In specific embodiments, steps (a) and (b) may be repeated at least 1, 2, 3, 4, or 5 or more times as desired. The invention still further provides a soybean plant produced by this and the foregoing methods.

DETAILED DESCRIPTION OF THE INVENTION

The instant invention provides methods and composition relating to plants, seeds and derivatives of the soybean variety A1026138. Soybean variety A1026138 is adapted to mid group 2 growing regions. Soybean variety A1026138 was developed from an initial cross of 3015806-01/ ((AJW2504H0C:@.@.~/~@.@.@.~/~)*2/MON89788:@>0002.). The breeding history of the variety can be summarized as follows:

| Generation | Year | Description |
|---|---|---|
| Cross | 2006 | The cross was made at Janesville, WI |
| $F_1$ | 2006 | Plants were grown at Isabela, PR and advanced using bulk |
| $F_2$ | 2007 | Plants were grown at Isabela, PR and advanced using single plant selection |
| $F_3$ | 2007 | Plants were grown at Janesville, WI and advanced using single plant selection |
| $F_4$ | 2008 | Plants were grown in Janesville, WI in progeny row yield trials and the variety A1026138 was selected based on the agronomic characteristics, including but not limited to, general plant health, lodging, early emergence, and general disease resistance, including PRR, SCN, etc. |

| | | Yield Testing | | |
|---|---|---|---|---|
| Generation | Year | No. of Locations | Rank | No. of Entries |
| $F_5$ | 2009 | 6 | 4 | 60 |
| $F_6$ | 2010 | 33 | 7 | 70 |

The soybean variety A1026138 has been judged to be uniform for breeding purposes and testing. The variety A1026138 can be reproduced by planting and growing seeds of the variety under self-pollinating or sib-pollinating conditions, as is known to those of skill in the agricultural arts. Variety A1026138 shows no variants other than what would normally be expected due to environment or that would occur for almost any characteristic during the course of repeated sexual reproduction.

The results of an objective evaluation of the variety are presented below, in Table 1. Those of skill in the art will recognize that these are typical values that may vary due to environment and that other values that are substantially equivalent are within the scope of the invention.

TABLE 1

Phenotypic Description of A1026138

| Trait | Phenotype |
|---|---|
| Morphology: | |
| Relative Maturity | 2.4 |
| Flower Color | Purple |
| Pubescence Color | Tawny |
| Hilum Color | Black |
| Pod Color | Tan |
| Hypocotyl Color | Purple |
| Seed Luster | Dull |
| Seed Shape | Spherical flattened |
| Leaf Shape | Ovate |
| Leaf Color | Green |
| Canopy | Intermediate |
| Growth Habit | Indeterminate |
| Disease Reactions: | |
| *Phytophthora* Reaction & Allele | Rps1c |
| SCN Race 3 Reaction | Resistant |
| Brown Stem Rot | Resistant |
| Herbicide Reactions: | |
| Glyphosate | Resistant, MON89788 |
| Sulfonylurea | Susceptible |

The performance characteristics of soybean variety A1026138 were also analyzed and comparisons were made with selected varieties. The results of the analysis are presented below, in Table 2.

TABLE 2

Exemplary Agronomic Traits of A1026138 vs Selected and Competing Varieties

| Entries Compared | YLD_BE | MAT | PHT | LDG | PSC | EMR | SDV | PRO | OIL | SWT | IDC |
|---|---|---|---|---|---|---|---|---|---|---|---|
| A1026138 | 56.7 | 20.5 | 37.8 | 2 | 3.1 | 2 | 2 | 40.5 | 21.4 | 3,030 | 4.5 |
| AG1931 | 53.4 | 13 | 32.8 | 2.6 | 3.3 | 2.6 | 3.5 | 42.6 | 21.2 | 3,174.7 | 3.3 |
| Deviation | 3.22 | 7.44 | 4.91 | −0.58 | −0.24 | −0.58 | −1.5 | −2.1 | 0.17 | −144.67 | 1.17 |
| Significance | ** | ** | * | | | + | | | | | |
| # Obs | 36 | 10 | 4 | 9 | 12 | 2 | 2 | 1 | 1 | 1 | 1 |

TABLE 2-continued

Exemplary Agronomic Traits of A1026138 vs Selected and Competing Varieties

| Entries Compared | YLD_BE | MAT | PHT | LDG | PSC | EMR | SDV | PRO | OIL | SWT | IDC |
|---|---|---|---|---|---|---|---|---|---|---|---|
| Years | 2 | 2 | 1 | 1 | 2 | 1 | 1 | 1 | 1 | 1 | 1 |
| Win Percent | 81 | 0 | 0 | 88 | 50 | 100 | 100 | 0 | 100 | 0 | 0 |
| Test Mean | 52.2 | 16.9 | 34.7 | 2.7 | 4.1 | 3.2 | 3.2 | 42.2 | 21.4 | 2,823.3 | 3.4 |
| A1026138 | 56.1 | 20.3 | 36.6 | 2.3 | 3.1 | 2 | 2 | 39.3 | 21.3 | | 4.5 |
| AG2002 | 51.7 | 15.8 | 32.2 | 2.8 | 3.7 | 4 | 4 | 38.5 | 22.1 | | 3.5 |
| Deviation | 4.34 | 4.45 | 4.37 | −0.47 | −0.58 | −2 | −2 | 0.8 | −0.8 | | 1 |
| Significance | ** | ** | | + | + | | ** | | | | |
| # Obs | 33 | 11 | 5 | 6 | 12 | 2 | 2 | 1 | 1 | | 1 |
| Years | 2 | 2 | 2 | 1 | 2 | 1 | 1 | 1 | 1 | 1 | 1 |
| Win Percent | 88 | 0 | 0 | 100 | 78 | 100 | 100 | 100 | 0 | | 0 |
| Test Mean | 51.8 | 17.7 | 33.9 | 3 | 4 | 3.3 | 3.2 | 39.7 | 21.4 | | 3.4 |
| A1026138 | 56.5 | 19.5 | 37.6 | 2 | 3.1 | 2 | 2 | 40.5 | 21 | 3,016.5 | 4.5 |
| AG2031 | 54.6 | 14.1 | 34.6 | 2.2 | 4 | 3.3 | 3 | 41.8 | 21.4 | 2,608 | 4 |
| Deviation | 1.93 | 5.44 | 3.03 | −0.24 | −0.91 | −1.32 | −1 | −1.3 | −0.35 | 408.54 | 0.5 |
| Significance | * | ** | * | | ** | | ** | * | | * | |
| # Obs | 37 | 13 | 5 | 11 | 12 | 2 | 2 | 4 | 4 | 4 | 1 |
| Years | 2 | 2 | 1 | 1 | 2 | 1 | 1 | 1 | 1 | 1 | 1 |
| Win Percent | 70 | 0 | 0 | 70 | 91 | 100 | 100 | 0 | 25 | 100 | 0 |
| Test Mean | 52.3 | 16.3 | 35.2 | 2.5 | 4 | 3.3 | 3.2 | 41.5 | 21.3 | 2,846 | 3.6 |
| A1026138 | 56.1 | 19.1 | 37.8 | 2.6 | 3.1 | 2 | 2 | 40.5 | 21 | 3,016.5 | 4.5 |
| AG2041V | 52 | 13.2 | 34 | 3 | 3.9 | 3.3 | 3.8 | 42.4 | 21.4 | 2,812 | 4 |
| Deviation | 4.02 | 5.92 | 3.75 | −0.4 | −0.86 | −1.25 | −1.75 | −1.88 | −0.33 | 204.5 | 0.5 |
| Significance | ** | ** | + | + | * | | + | * | | | |
| # Obs | 31 | 6 | 4 | 5 | 12 | 2 | 2 | 4 | 4 | 4 | 1 |
| Years | 2 | 1 | 1 | 1 | 2 | 1 | 1 | 1 | 1 | 1 | 1 |
| Win Percent | 81 | 0 | 0 | 100 | 90 | 100 | 100 | 0 | 25 | 100 | 0 |
| Test Mean | 52.6 | 15.7 | 34.1 | 3.4 | 4.1 | 3.4 | 3.2 | 41.4 | 21.4 | 2,855.4 | 3.6 |
| A1026138 | 56.9 | 21 | 36.6 | 2.1 | 3.1 | 2 | 2 | 40 | 21 | 3,030 | 4.5 |
| AG2107 | 50.9 | 16 | 31 | 2.2 | 4.2 | 3.8 | 3 | 41.1 | 22.2 | 2,904 | 3.7 |
| Deviation | 5.96 | 4.92 | 5.59 | −0.05 | −1.11 | −1.75 | −1 | −1.11 | −1.1 | 126 | 0.83 |
| Significance | ** | ** | * | | ** | | ** | | | | |
| # Obs | 36 | 12 | 5 | 8 | 12 | 2 | 2 | 2 | 2 | 1 | 1 |
| Years | 2 | 2 | 2 | 1 | 2 | 1 | 1 | 2 | 2 | 1 | 1 |
| Win Percent | 92 | 0 | 0 | 60 | 100 | 100 | 100 | 0 | 0 | 100 | 0 |
| Test Mean | 52.8 | 17.6 | 33.8 | 2.8 | 4 | 3.3 | 3.2 | 41.4 | 21.1 | 2,844.7 | 3.4 |
| A1026138 | 56.5 | 20.1 | 36.6 | 2 | 3.1 | 2 | 2 | 39.4 | 21 | | 4.5 |
| AG2108 | 53.2 | 16.8 | 31.2 | 1.7 | 3.8 | 3.2 | 3 | 39 | 22 | | 3.9 |
| Deviation | 3.27 | 3.27 | 5.36 | 0.27 | −0.7 | −1.15 | −1 | 0.44 | −0.99 | | 0.58 |
| Significance | ** | ** | | | * | | ** | | + | | |
| # Obs | 39 | 15 | 5 | 11 | 12 | 2 | 2 | 2 | 2 | | 1 |
| Years | 2 | 2 | 2 | 1 | 2 | 1 | 1 | 1 | 1 | | 1 |
| Win Percent | 82 | 0 | 0 | 38 | 83 | 100 | 100 | 50 | 0 | | 0 |
| Test Mean | 52.2 | 17.1 | 34.3 | 2.5 | 4.1 | 3.1 | 3.2 | 40.1 | 21.2 | | 3.4 |
| A1026138 | 56.5 | 19.9 | 37.6 | 2 | 3.1 | 2 | 2 | 40.5 | 21 | 3,016.5 | 4.5 |
| AG2131 | 50.8 | 13.7 | 36.2 | 4.3 | 4.9 | 3.6 | 3 | 42.2 | 21.3 | 2,456.4 | 2.4 |
| Deviation | 5.67 | 6.18 | 1.4 | −2.35 | −1.82 | −1.65 | −1 | −1.65 | −0.31 | 560.08 | 2.11 |
| Significance | ** | ** | | ** | ** | | ** | * | | ** | |
| # Obs | 39 | 14 | 5 | 11 | 12 | 2 | 2 | 4 | 4 | 4 | 1 |
| Years | 2 | 2 | 1 | 1 | 2 | 1 | 1 | 1 | 1 | 1 | 1 |
| Win Percent | 82 | 0 | 20 | 100 | 100 | 100 | 100 | 0 | 25 | 100 | 0 |
| Test Mean | 53 | 17.7 | 35 | 2.7 | 4 | 3.4 | 3.2 | 41.5 | 21.3 | 2,858 | 3.6 |
| A1026138 | 56.5 | 20.1 | 36.7 | 2 | 3.1 | 2 | 2 | 40.3 | 21.1 | 3,016.5 | 4.5 |
| AG2130 | 53 | 17 | 33.1 | 1.8 | 3.2 | 2.8 | 2.8 | 40.7 | 20.9 | 3,163.7 | 3.5 |
| Deviation | 3.48 | 3.06 | 3.55 | 0.17 | −0.13 | −0.75 | −0.83 | −0.4 | 0.16 | −147.17 | 1 |
| Significance | ** | ** | * | | | | | | | | |
| # Obs | 39 | 15 | 6 | 11 | 12 | 2 | 2 | 5 | 5 | 4 | 1 |
| Years | 2 | 2 | 2 | 1 | 2 | 1 | 1 | 2 | 2 | 1 | 1 |
| Win Percent | 87 | 0 | 0 | 67 | 55 | 100 | 100 | 20 | 60 | 25 | 0 |
| Test Mean | 52 | 18.3 | 34.6 | 2.6 | 4.2 | 3.2 | 3.2 | 41 | 21.4 | 2,858 | 3.6 |
| A1026138 | 56.5 | 19.1 | 37.8 | 2.6 | 2.9 | 2 | 2 | | | | 4.5 |
| AG2204 | 52.1 | 15 | 30 | 2.7 | 4.1 | 2 | 3 | | | | 4.7 |
| Deviation | 4.4 | 4.1 | 7.75 | −0.1 | −1.17 | 0 | −1 | | | | −0.17 |
| Significance | * | * | * | | + | | | | | | |
| # Obs | 25 | 5 | 4 | 5 | 9 | 2 | 2 | | | | 1 |
| Years | 1 | 1 | 1 | 1 | 1 | 1 | 1 | | | | 1 |
| Win Percent | 88 | 0 | 0 | 50 | 86 | — | 100 | | | | 100 |
| Test Mean | 53.9 | 16.5 | 34.5 | 3.4 | 4 | 3.3 | 3.2 | | | | 3.4 |
| A1026138 | 56.2 | 20.9 | 36.6 | 2.6 | 3.2 | 2 | 2 | 40.2 | 21 | 3,016.5 | 4.5 |
| AG2222V | 47 | 16.9 | 30 | 2.3 | 4.8 | 4.5 | 3.3 | 40.2 | 22.3 | 3,019.3 | 4.6 |
| Deviation | 9.26 | 4.08 | 6.57 | 0.32 | −1.66 | −2.5 | −1.25 | −0.1 | −1.25 | −2.75 | −0.08 |
| Significance | ** | ** | ** | | * | | | | ** | | |
| # Obs | 34 | 8 | 5 | 5 | 11 | 2 | 2 | 6 | 6 | 4 | 1 |
| Years | 2 | 2 | 2 | 1 | 2 | 1 | 1 | 2 | 2 | 1 | 1 |
| Win Percent | 88 | 0 | 0 | 33 | 91 | 100 | 100 | 33 | 0 | 33 | 100 |
| Test Mean | 52.5 | 19.3 | 33.6 | 3.3 | 4.3 | 3.4 | 3.2 | 40.9 | 21.3 | 2,855.4 | 3.6 |
| A1026138 | 56.7 | 20.6 | 37.8 | 2.6 | 3 | 2 | 2 | | | | 4.5 |

TABLE 2-continued

Exemplary Agronomic Traits of A1026138 vs Selected and Competing Varieties

| Entries Compared | YLD_BE | MAT | PHT | LDG | PSC | EMR | SDV | PRO | OIL | SWT | IDC |
|---|---|---|---|---|---|---|---|---|---|---|---|
| AG2403 | 51 | 16.9 | 31.4 | 1.8 | 4.4 | 3.1 | 3.8 | | | | 3.2 |
| Deviation | 5.64 | 3.79 | 6.38 | 0.8 | −1.47 | −1.12 | −1.75 | | | | 1.33 |
| Significance | ** | ** | ** | + | * | | + | | | | |
| # Obs | 34 | 7 | 4 | 5 | 10 | 2 | 2 | | | | 1 |
| Years | 2 | 2 | 1 | 1 | 2 | 1 | 1 | | | | 1 |
| Win Percent | 85 | 0 | 0 | 0 | 89 | 100 | 100 | | | | 0 |
| Test Mean | 53 | 19.2 | 34.7 | 3.3 | 4 | 3.3 | 3.1 | | | | 3.5 |
| A1026138 | 56.9 | 20.6 | 37.8 | 2.6 | 3 | 2 | 2 | | | | 4.5 |
| AG2406 | 50.7 | 17.9 | 35.6 | 2.2 | 3 | 3.6 | 3.3 | | | | 3.9 |
| Deviation | 6.18 | 2.74 | 2.12 | 0.4 | 0 | −1.62 | −1.25 | | | | 0.58 |
| Significance | ** | * | + | | | | | | | | |
| # Obs | 33 | 7 | 4 | 5 | 10 | 2 | 2 | | | | 1 |
| Years | 2 | 2 | 1 | 1 | 2 | 1 | 1 | | | | 1 |
| Win Percent | 88 | 14 | 0 | 33 | 57 | 100 | 100 | | | | 0 |
| Test Mean | 53.3 | 19.4 | 34.7 | 3.3 | 4 | 3.3 | 3.1 | | | | 3.5 |
| A1026138 | 56.5 | 19.9 | 37.6 | 2 | 3.1 | 2 | 2 | 40.5 | 21 | 3,016.5 | 4.5 |
| AG2430 | 54 | 19.6 | 34.9 | 2 | 3.7 | 2.9 | 4 | 40 | 21.9 | 3,186.4 | 3.1 |
| Deviation | 2.53 | 0.29 | 2.74 | −0.01 | −0.58 | −0.87 | −2 | 0.5 | −0.88 | −169.88 | 1.39 |
| Significance | ** | | + | | + | | | | * | | |
| # Obs | 38 | 14 | 5 | 11 | 12 | 2 | 2 | 4 | 4 | 4 | 1 |
| Years | 2 | 2 | 1 | 1 | 2 | 1 | 1 | 1 | 1 | 1 | 1 |
| Win Percent | 74 | 50 | 0 | 67 | 82 | 100 | 100 | 50 | 0 | 33 | 0 |
| Test Mean | 52.8 | 19.3 | 35.4 | 2.6 | 4.1 | 2.8 | 3.1 | 41.4 | 21.4 | 2,889.1 | 3.5 |
| A1026138 | 56.4 | 19.5 | 37.6 | 2 | 3.1 | 2 | 2 | 40.5 | 21 | 3,016.5 | 4.5 |
| AG2431 | 58 | 19 | 33.1 | 2 | 3.1 | 1.6 | 2.9 | 40.8 | 21.4 | 2,765 | 4.4 |
| Deviation | −1.57 | 0.49 | 4.5 | −0.02 | 0.03 | 0.44 | −0.88 | −0.23 | −0.42 | 251.46 | 0.12 |
| Significance | | | ** | | | + | | | + | + | |
| # Obs | 34 | 13 | 5 | 11 | 11 | 2 | 2 | 4 | 4 | 4 | 1 |
| Years | 2 | 2 | 1 | 1 | 1 | 1 | 1 | 1 | 1 | 1 | 1 |
| Win Percent | 38 | 27 | 0 | 57 | 44 | 0 | 100 | 50 | 25 | 100 | 0 |
| Test Mean | 53.3 | 18.3 | 35.1 | 2.7 | 4 | 3.4 | 3.2 | 41.4 | 21.4 | 2,864 | 3.6 |
| A1026138 | 56.2 | 20.4 | 36.6 | 2.6 | 3.2 | 2 | 2 | 40.3 | 21 | 3,016.5 | 4.5 |
| AG2440V | 53.2 | 21.1 | 33.1 | 3.3 | 4 | 2.4 | 3.2 | 41.4 | 20.4 | 2,863 | 3.7 |
| Deviation | 3.04 | −0.69 | 3.52 | −0.68 | −0.82 | −0.44 | −1.17 | −1.04 | 0.6 | 153.5 | 0.78 |
| Significance | * | | ** | * | | | + | ** | * | | |
| # Obs | 34 | 7 | 5 | 5 | 11 | 2 | 2 | 5 | 5 | 4 | 1 |
| Years | 2 | 2 | 2 | 1 | 2 | 1 | 1 | 2 | 2 | 1 | 1 |
| Win Percent | 74 | 67 | 0 | 100 | 78 | 100 | 100 | 0 | 100 | 100 | 0 |
| Test Mean | 52.1 | 19.5 | 33.8 | 3.3 | 4.3 | 2.9 | 3.2 | 41.3 | 21.2 | 2,855.4 | 3.7 |
| A1026138 | 56.4 | 20.9 | 36.6 | 2.6 | 3.2 | 2 | 2 | 40.2 | 21 | 3,016.5 | 4.5 |
| AG2522V | 52.3 | 21.8 | 32.9 | 3.8 | 4.3 | 5.3 | 3.3 | 41.3 | 20.8 | 2,504 | 3.9 |
| Deviation | 4.08 | −0.82 | 3.68 | −1.17 | −1.12 | −3.33 | −1.25 | −1.13 | 0.24 | 512.5 | 0.58 |
| Significance | ** | | * | + | * | | ** | + | | ** | |
| # Obs | 34 | 8 | 5 | 5 | 11 | 2 | 2 | 6 | 6 | 4 | 1 |
| Years | 2 | 2 | 2 | 1 | 2 | 1 | 1 | 2 | 2 | 1 | 1 |
| Win Percent | 82 | 62 | 0 | 100 | 78 | 100 | 100 | 17 | 67 | 100 | 0 |
| Test Mean | 53.2 | 19.6 | 33.9 | 3.4 | 4.2 | 3.3 | 3.1 | 40.9 | 21.3 | 2,855.4 | 3.7 |
| A1026138 | 56.5 | 19.9 | 37.6 | 2 | 3.1 | 2 | 2 | 40.5 | 21 | 3,016.5 | 4.5 |
| AG2531 | 53.3 | 17.2 | 35.6 | 2.8 | 4.2 | 3.2 | 3.3 | 41.6 | 21.3 | 3,029.3 | 3.7 |
| Deviation | 3.23 | 2.63 | 1.97 | −0.79 | −1.08 | −1.24 | −1.25 | −1.07 | −0.24 | −12.75 | 0.78 |
| Significance | ** | ** | * | ** | ** | | | + | | | |
| # Obs | 38 | 14 | 5 | 11 | 12 | 2 | 2 | 4 | 4 | 4 | 1 |
| Years | 2 | 2 | 1 | 1 | 2 | 1 | 1 | 1 | 1 | 1 | 1 |
| Win Percent | 76 | 0 | 0 | 100 | 100 | 100 | 100 | 0 | 25 | 33 | 0 |
| Test Mean | 53.2 | 19.4 | 35.4 | 2.7 | 4.1 | 3 | 3.2 | 41.4 | 21.4 | 2,864 | 3.6 |
| A1026138 | 56.5 | 19.9 | 37.6 | 2 | 3.1 | 2 | 2 | 40.5 | 21 | 3,016.5 | 4.5 |
| AG2530 | 52.9 | 18.5 | 37.2 | 2.6 | 3.8 | 3.5 | 2.9 | 41.3 | 20.3 | 3,135.3 | 3.1 |
| Deviation | 3.62 | 1.32 | 0.44 | −0.63 | −0.75 | −1.45 | −0.94 | −0.81 | 0.77 | −118.75 | 1.38 |
| Significance | ** | + | | + | * | | | * | ** | | |
| # Obs | 38 | 14 | 5 | 11 | 12 | 2 | 2 | 4 | 4 | 4 | 1 |
| Years | 2 | 2 | 1 | 1 | 2 | 1 | 1 | 1 | 1 | 1 | 1 |
| Win Percent | 76 | 21 | 60 | 80 | 73 | 100 | 100 | 0 | 100 | 25 | 0 |
| Test Mean | 52.4 | 19.3 | 35.5 | 2.6 | 4.2 | 3.1 | 3.3 | 41.4 | 21.4 | 2,889.1 | 3.5 |
| A1026138 | 56.6 | 20.4 | 36.6 | 2.6 | 3.2 | 2 | 2 | 39.4 | 21 | | 4.5 |
| AG2622V | 51.6 | 23.9 | 32 | 3.5 | 5.1 | 3 | 2.7 | 39.6 | 20.8 | | 4.1 |
| Deviation | 5.02 | −3.54 | 4.6 | −0.94 | −1.94 | −0.96 | −0.67 | −0.17 | 0.21 | | 0.44 |
| Significance | ** | ** | + | | ** | | ** | | | | |
| # Obs | 35 | 7 | 5 | 5 | 11 | 2 | 2 | 2 | 2 | | 1 |
| Years | 2 | 2 | 2 | 1 | 2 | 1 | 1 | 1 | 1 | | 1 |
| Win Percent | 89 | 100 | 0 | 100 | 91 | 100 | 100 | 50 | 50 | | 0 |
| Test Mean | 52.5 | 19.6 | 34.3 | 3.3 | 4.3 | 3.1 | 3.1 | 39.9 | 21.1 | | 3.6 |
| A1026138 | 56.2 | 19.1 | 37.6 | 2 | 3.1 | 2 | 2 | 40.5 | 21 | 3,016.5 | 4.5 |
| AG2631 | 52.1 | 21.1 | 37.1 | 3.4 | 4.6 | 3.7 | 3.2 | 42.9 | 21 | 2,828.3 | 3.7 |
| Deviation | 4.09 | −2.03 | 0.48 | −1.4 | −1.56 | −1.65 | −1.2 | −2.38 | 0.05 | 188.25 | 0.8 |
| Significance | ** | ** | | ** | ** | | ** | | | | |
| # Obs | 34 | 12 | 5 | 11 | 11 | 2 | 2 | 4 | 4 | 4 | 1 |

TABLE 2-continued

Exemplary Agronomic Traits of A1026138 vs Selected and Competing Varieties

| Entries Compared | YLD_BE | MAT | PHT | LDG | PSC | EMR | SDV | PRO | OIL | SWT | IDC |
|---|---|---|---|---|---|---|---|---|---|---|---|
| Years | 2 | 1 | 1 | 1 | 1 | 1 | 1 | 1 | 1 | 1 | 1 |
| Win Percent | 76 | 92 | 40 | 100 | 100 | 100 | 100 | 0 | 75 | 100 | 0 |
| Test Mean | 52.9 | 19.2 | 35.6 | 2.8 | 4.2 | 3.2 | 3.2 | 41.3 | 21.5 | 2,873.2 | 3.6 |
| A1026138 | 56.5 | 19.1 | 37.6 | 2 | 3.3 | 2 | 2 | 40.5 | 21 | 3,016.5 | 4.5 |
| AG2632 | 57.1 | 22.1 | 36.8 | 2.3 | 3.4 | 2.8 | 3.5 | 41.4 | 21.2 | 2,948.8 | 3.7 |
| Deviation | −0.61 | −3 | 0.8 | −0.27 | −0.1 | −0.75 | −1.5 | −0.88 | −0.18 | 67.75 | 0.83 |
| Significance |  | ** |  |  |  |  |  |  |  |  |  |
| # Obs | 33 | 12 | 5 | 11 | 10 | 2 | 2 | 4 | 4 | 4 | 1 |
| Years | 1 | 1 | 1 | 1 | 1 | 1 | 1 | 1 | 1 | 1 | 1 |
| Win Percent | 45 | 92 | 0 | 71 | 57 | 100 | 100 | 25 | 25 | 67 | 0 |
| Test Mean | 53.6 | 16.7 | 36.2 | 2.8 | 4.2 | 3.5 | 3.1 | 41.3 | 21.5 | 2,873.2 | 3.5 |
| A1026138 | 56.5 | 19.9 | 37.6 | 2 | 3.1 | 2 | 2 | 40.6 | 21.1 | 3,039.3 | 4.5 |
| AG2731 | 55.7 | 21.9 | 38.7 | 1.9 | 3.8 | 4.2 | 3.1 | 42.4 | 20.9 | 2,680 | 3.7 |
| Deviation | 0.87 | −2.04 | −1.13 | 0.11 | −0.74 | −2.18 | −1.12 | −1.87 | 0.13 | 359.33 | 0.75 |
| Significance |  | ** |  |  | * |  | + | * |  |  |  |
| # Obs | 38 | 14 | 5 | 11 | 12 | 2 | 2 | 3 | 3 | 3 | 1 |
| Years | 2 | 2 | 1 | 1 | 2 | 1 | 1 | 1 | 1 | 1 | 1 |
| Win Percent | 63 | 92 | 75 | 57 | 89 | 100 | 100 | 0 | 67 | 100 | 0 |
| Test Mean | 53.5 | 19.1 | 36.4 | 2.9 | 4 | 3.3 | 3.3 | 41.5 | 21.5 | 2,842.1 | 3.6 |
| A1026138 | 56.4 | 19.1 | 37.8 | 2.6 | 3.2 | 2 | 2 | 40.5 | 21 | 3,016.5 | 4.5 |
| AG2740V | 53.6 | 26 | 38.4 | 2.9 | 4.3 | 2.7 | 3.1 | 41.9 | 20.6 | 2,609.5 | 3.9 |
| Deviation | 2.78 | −6.91 | −0.65 | −0.25 | −1.11 | −0.72 | −1.12 | −1.4 | 0.47 | 407 | 0.58 |
| Significance | + | ** |  |  | * |  | + | ** | * | ** |  |
| # Obs | 28 | 5 | 4 | 5 | 10 | 2 | 2 | 4 | 4 | 4 | 1 |
| Years | 1 | 1 | 1 | 1 | 1 | 1 | 1 | 1 | 1 | 1 | 1 |
| Win Percent | 79 | 100 | 75 | 75 | 100 | 100 | 100 | 0 | 100 | 100 | 0 |
| Test Mean | 53.3 | 18.1 | 34.5 | 3.3 | 4.3 | 2.9 | 3.1 | 41.4 | 21.4 | 2,855.4 | 3.7 |
| A1026138 | 56.7 | 20.5 | 37.8 | 2 | 2.9 | 2 | 2 | 41 | 20.6 | 2,841 | 4.5 |
| CR2 1906N | 50.2 | 12.8 | 32.8 | 2.5 | 4.1 | 2.8 | 3.5 | 39.7 | 22.7 | 2,392 | 1.5 |
| Deviation | 6.42 | 7.64 | 4.92 | −0.48 | −1.22 | −0.75 | −1.5 | 1.3 | −2.1 | 449 | 3 |
| Significance | ** | ** | + | * | ** |  |  |  |  |  |  |
| # Obs | 36 | 10 | 4 | 9 | 11 | 2 | 2 | 1 | 1 | 1 | 1 |
| Years | 2 | 2 | 1 | 1 | 2 | 1 | 1 | 1 | 1 | 1 | 1 |
| Win Percent | 92 | 0 | 0 | 86 | 100 | 100 | 100 | 100 | 0 | 100 | 0 |
| Test Mean | 52.9 | 16.4 | 34.6 | 2.7 | 3.8 | 3.3 | 3.2 | 41.1 | 21.4 | 2,927.5 | 3.4 |
| A1026138 | 56.9 | 20.6 | 37.8 | 2.1 | 3.1 | 2 | 2 | 40.8 | 21 | 2,935.5 | 4.5 |
| CR2 1933 | 55.4 | 16.9 | 34.1 | 2.6 | 3.3 | 1.8 | 2.5 | 42.1 | 21.7 | 2,762 | 3.3 |
| Deviation | 1.52 | 3.76 | 3.62 | −0.46 | −0.22 | 0.25 | −0.5 | −1.3 | −0.7 | 173.5 | 1.17 |
| Significance |  | ** |  |  |  |  |  |  |  |  |  |
| # Obs | 31 | 9 | 4 | 8 | 11 | 2 | 2 | 2 | 2 | 2 | 1 |
| Years | 2 | 2 | 1 | 1 | 1 | 1 | 1 | 1 | 1 | 1 | 1 |
| Win Percent | 71 | 0 | 0 | 67 | 60 | 50 | 100 | 0 | 0 | 100 | 0 |
| Test Mean | 53.6 | 16.4 | 34.5 | 2.8 | 4 | 3.3 | 3.2 | 41.6 | 21.5 | 2,866.1 | 3.4 |
| A1026138 | 56.5 | 19.5 | 37.6 | 2 | 3.1 | 2 | 2 | 40.5 | 21 | 3,016.5 | 4.5 |
| CR2 2003N | 52.5 | 13.4 | 33.6 | 3.4 | 4.2 | 2.8 | 3.2 | 41.1 | 21.3 | 3,209.8 | 3.4 |
| Deviation | 4.03 | 6.15 | 4.02 | −1.38 | −1.15 | −0.75 | −1.17 | −0.6 | −0.28 | −193.29 | 1.06 |
| Significance | ** | ** | * | ** | ** |  | + |  |  | + |  |
| # Obs | 37 | 13 | 5 | 11 | 12 | 2 | 2 | 4 | 4 | 4 | 1 |
| Years | 2 | 2 | 1 | 1 | 2 | 1 | 1 | 1 | 1 | 1 | 1 |
| Win Percent | 78 | 0 | 0 | 100 | 92 | 100 | 100 | 25 | 25 | 0 | 0 |
| Test Mean | 53.1 | 16.7 | 34.8 | 2.6 | 4 | 3.4 | 3.2 | 41.4 | 21.4 | 2,862 | 3.6 |
| A1026138 | 56.8 | 20.5 | 37.8 | 2.1 | 2.9 | 2 | 2 | 40.5 | 21.4 | 3,030 | 4.5 |
| CR2 2023N | 54.9 | 14.2 | 29.4 | 2.3 | 3.4 | 4.3 | 2.5 | 42.6 | 21.3 | 3,030 | 2.7 |
| Deviation | 1.86 | 6.24 | 8.31 | −0.19 | −0.5 | −2.25 | −0.5 | −2.1 | 0.1 | 0 | 1.83 |
| Significance |  | ** | * |  |  |  |  |  |  |  |  |
| # Obs | 33 | 10 | 4 | 8 | 11 | 2 | 2 | 1 | 1 | 1 | 1 |
| Years | 2 | 2 | 1 | 1 | 2 | 1 | 1 | 1 | 1 | 1 | 1 |
| Win Percent | 70 | 0 | 0 | 100 | 75 | 100 | 100 | 0 | 100 | — | 0 |
| Test Mean | 53.4 | 17.4 | 34.4 | 2.8 | 3.9 | 3.3 | 3.2 | 42 | 21.3 | 2,870.1 | 3.4 |
| A1026138 | 56.5 | 21 | 36.6 | 2.1 | 3.1 | 2 | 2 | 39.9 | 20.9 | 2,841 | 4.5 |
| CR2 2100 | 53.2 | 16.6 | 30 | 2.2 | 3.8 | 3.5 | 3.5 | 40.7 | 21 | 3,030 | 3.8 |
| Deviation | 3.28 | 4.33 | 6.63 | −0.12 | −0.73 | −1.5 | −1.5 | −0.74 | −0.13 | −189 | 0.67 |
| Significance | ** | ** | * |  | * |  |  |  |  |  |  |
| # Obs | 36 | 12 | 5 | 8 | 12 | 2 | 2 | 3 | 3 | 1 | 1 |
| Years | 2 | 2 | 2 | 1 | 2 | 1 | 1 | 2 | 2 | 1 | 1 |
| Win Percent | 81 | 8 | 0 | 60 | 83 | 100 | 100 | 33 | 50 | 0 | 0 |
| Test Mean | 52.2 | 17.6 | 34.2 | 2.7 | 4.1 | 3.3 | 3.2 | 40.4 | 21.2 | 2,927.5 | 3.4 |
| A1026138 | 56.7 | 20.5 | 37.8 | 2.1 | 2.9 | 2 | 2 | 40.5 | 21.4 | 3,030 | 4.5 |
| CR2 2103 | 54.4 | 19.1 | 36.4 | 2.9 | 4.5 | 2.8 | 3.5 | 42.4 | 20.8 | 3,030 | 2.7 |
| Deviation | 2.3 | 1.33 | 1.31 | −0.75 | −1.65 | −0.75 | −1.5 | −1.9 | 0.6 | 0 | 1.83 |
| Significance | + |  |  | + | ** |  |  |  |  |  |  |
| # Obs | 30 | 10 | 4 | 8 | 10 | 2 | 2 | 1 | 1 | 1 | 1 |
| Years | 2 | 2 | 1 | 1 | 1 | 1 | 1 | 1 | 1 | 1 | 1 |
| Win Percent | 67 | 20 | 33 | 86 | 100 | 100 | 100 | 0 | 100 | — | 0 |
| Test Mean | 53.6 | 17.6 | 34.4 | 2.8 | 3.9 | 3.3 | 3.2 | 42 | 21.3 | 2,870.1 | 3.4 |
| A1026138 | 56.7 | 20.6 | 37.8 | 2.1 | 2.9 | 2 | 2 | 40.5 | 21.4 | 3,030 | 4.5 |

TABLE 2-continued

Exemplary Agronomic Traits of A1026138 vs Selected and Competing Varieties

| Entries Compared | YLD_BE | MAT | PHT | LDG | PSC | EMR | SDV | PRO | OIL | SWT | IDC |
|---|---|---|---|---|---|---|---|---|---|---|---|
| CR2 2301N | 55.1 | 18.4 | 33.3 | 2.7 | 3.6 | 2.5 | 3.5 | 43.2 | 20.5 | 3,030 | 4.3 |
| Deviation | 1.62 | 2.17 | 4.44 | −0.56 | −0.75 | −0.5 | −1.5 | −2.7 | 0.9 | 0 | 0.17 |
| Significance |  | + | * | + | + |  |  |  |  |  |  |
| # Obs | 30 | 9 | 4 | 8 | 10 | 2 | 2 | 1 | 1 | 1 | 1 |
| Years | 2 | 2 | 1 | 1 | 1 | 1 | 1 | 1 | 1 | 1 | 1 |
| Win Percent | 67 | 11 | 0 | 83 | 80 | 50 | 100 | 0 | 100 | — | 0 |
| Test Mean | 53.7 | 18.6 | 34.4 | 2.8 | 3.9 | 3.3 | 3.2 | 42.3 | 21 | 2,856 | 3.4 |
| A1026138 | 56.4 | 19.5 | 37.6 | 2 | 3.1 | 2 | 2 | 40.5 | 21 | 3,016.5 | 4.5 |
| CR2 2302N | 53.5 | 16.8 | 34.2 | 3.4 | 4.3 | 2.4 | 3.5 | 41.8 | 21.3 | 2,909 | 4.2 |
| Deviation | 2.89 | 2.72 | 3.37 | −1.38 | −1.18 | −0.42 | −1.5 | −1.27 | −0.31 | 107.5 | 0.33 |
| Significance | * | ** | ** | * | * |  | + | * |  |  |  |
| # Obs | 34 | 13 | 5 | 11 | 11 | 2 | 2 | 4 | 4 | 4 | 1 |
| Years | 2 | 2 | 1 | 1 | 1 | 1 | 1 | 1 | 1 | 1 | 1 |
| Win Percent | 74 | 8 | 0 | 90 | 82 | 50 | 100 | 0 | 25 | 50 | 0 |
| Test Mean | 53.2 | 17.4 | 35.1 | 2.7 | 4 | 3.4 | 3.2 | 41.5 | 21.3 | 2,853.2 | 3.6 |
| A1026138 | 56.5 | 19.6 | 37.6 | 2.2 | 2.9 | 2 | 2 | 40.4 | 21.3 | 3,138.5 | 4.5 |
| CR2 2402N | 53.5 | 17 | 34.5 | 2.4 | 3.8 | 2.5 | 2.5 | 42.3 | 21 | 2,935.5 | 2.5 |
| Deviation | 2.99 | 2.58 | 3.1 | −0.2 | −0.81 | −0.5 | −0.5 | −1.95 | 0.35 | 203 | 2 |
| Significance | * | ** | + |  |  | ** |  |  |  | * |  |
| # Obs | 32 | 12 | 5 | 9 | 9 | 2 | 2 | 2 | 2 | 2 | 1 |
| Years | 2 | 2 | 1 | 1 | 1 | 1 | 1 | 1 | 1 | 1 | 1 |
| Win Percent | 72 | 17 | 20 | 50 | 67 | 100 | 100 | 0 | 50 | 100 | 0 |
| Test Mean | 53.5 | 18.5 | 34.9 | 2.8 | 4.1 | 3.3 | 3.2 | 41.9 | 21.2 | 2,847.7 | 3.4 |
| A1026138 | 56.5 | 19.9 | 37.6 | 2 | 3.1 | 2 | 2 | 40.5 | 21 | 3,016.5 | 4.5 |
| CR2 2503N | 52.5 | 19.8 | 33.8 | 3.3 | 4.3 | 2.9 | 4.3 | 41.6 | 20.5 | 2,989.8 | 3.8 |
| Deviation | 4.04 | 0.02 | 3.84 | −1.27 | −1.23 | −0.9 | −2.25 | −1.05 | 0.52 | 26.75 | 0.71 |
| Significance | ** |  | * | ** | ** |  |  | + | + | + |  |
| # Obs | 38 | 14 | 5 | 11 | 12 | 2 | 2 | 4 | 4 | 4 | 1 |
| Years | 2 | 2 | 1 | 1 | 2 | 1 | 1 | 1 | 1 | 1 | 1 |
| Win Percent | 76 | 46 | 0 | 100 | 100 | 100 | 100 | 0 | 100 | 75 | 0 |
| Test Mean | 53.4 | 19.2 | 35.4 | 2.7 | 4.1 | 3.1 | 3.3 | 41.3 | 21.5 | 2,873.2 | 3.5 |
| A1026138 | 54 | 17 | 37 | 1.7 | 2 |  |  |  |  |  |  |
| CR2 2802N | 57.4 | 21 | 38.5 | 2 | 3.5 |  |  |  |  |  |  |
| Deviation | −3.36 | −4 | −1.5 | −0.33 | −1.5 |  |  |  |  |  |  |
| Significance |  | * |  |  |  |  |  |  |  |  |  |
| # Obs | 6 | 3 | 1 | 3 | 1 |  |  |  |  |  |  |
| Years | 1 | 1 | 1 | 1 | 1 |  |  |  |  |  |  |
| Win Percent | 33 | 100 | 100 | 100 | 100 |  |  |  |  |  |  |
| Test Mean | 54.3 | 19.3 | 37.9 | 1.9 | 2.8 |  |  |  |  |  |  |
| A1026138 | 56.2 | 19.8 | 36.6 | 2.6 | 3.1 | 2 | 2 | 40.3 | 21 | 3,016.5 | 4.5 |
| CR2 V2123N | 53.1 | 15.9 | 31.4 | 3.2 | 3.9 | 3.8 | 5 | 41.1 | 21 | 3,141.3 | 3.2 |
| Deviation | 3.06 | 3.84 | 5.2 | −0.64 | −0.84 | −1.79 | −3 | −0.77 | −0.04 | −124.75 | 1.33 |
| Significance | * | ** | * |  | * |  |  |  |  |  |  |
| # Obs | 31 | 7 | 5 | 5 | 12 | 2 | 2 | 5 | 5 | 4 | 1 |
| Years | 2 | 2 | 2 | 1 | 2 | 1 | 1 | 2 | 2 | 1 | 1 |
| Win Percent | 84 | 0 | 0 | 75 | 82 | 100 | 100 | 20 | 75 | 33 | 0 |
| Test Mean | 52.6 | 17.1 | 33.8 | 3.4 | 4.1 | 3.1 | 3.2 | 41.2 | 21.3 | 2,855.4 | 3.6 |
| A1026138 | 56.8 | 21 | 37.8 | 2.1 | 2.9 | 2 | 2 | 40.8 | 21 | 2,935.5 | 4.5 |
| CS 22R202N | 56.1 | 17.8 | 31.5 | 1.8 | 3.3 | 3 | 2.5 | 40.2 | 22.3 | 2,757.5 | 3 |
| Deviation | 0.75 | 3.14 | 6.25 | 0.34 | −0.41 | −1 | −0.5 | 0.6 | −1.25 | 178 | 1.5 |
| Significance |  | ** | * |  |  |  |  | ** | + |  |  |
| # Obs | 34 | 10 | 4 | 8 | 11 | 2 | 2 | 2 | 2 | 2 | 1 |
| Years | 2 | 2 | 1 | 1 | 2 | 1 | 1 | 1 | 1 | 1 | 1 |
| Win Percent | 59 | 0 | 0 | 0 | 75 | 100 | 100 | 100 | 0 | 100 | 0 |
| Test Mean | 53.8 | 18.4 | 34.4 | 2.8 | 3.8 | 3.3 | 3.2 | 41.6 | 21.4 | 2,898.8 | 3.4 |
| A1026138 | 56.8 | 19.9 | 37.6 | 2.2 | 3 | 2 | 2 | 40.2 | 21.2 | 3,247 | 4.5 |
| CS 24R202N | 55.2 | 20.4 | 35 | 3.1 | 4 | 4.3 | 3 | 41.5 | 21.5 | 2,841 | 2.5 |
| Deviation | 1.6 | −0.44 | 2.6 | −0.83 | −1.08 | −2.25 | −1 | −1.25 | −0.3 | 406 | 2 |
| Significance |  |  | + | + | * | ** |  |  |  |  |  |
| # Obs | 35 | 13 | 5 | 9 | 10 | 2 | 2 | 1 | 1 | 1 | 1 |
| Years | 2 | 2 | 1 | 1 | 2 | 1 | 1 | 1 | 1 | 1 | 1 |
| Win Percent | 69 | 67 | 0 | 83 | 88 | 100 | 100 | 0 | 0 | 100 | 0 |
| Test Mean | 53.6 | 18.6 | 34.9 | 2.9 | 4 | 3.3 | 3.2 | 41.5 | 21.2 | 2,851.1 | 3.4 |
| A1026138 | 56.4 | 20.4 | 37.8 | 2.6 | 2.9 | 2 | 2 |  |  |  | 4.5 |
| CSR2114 | 52.4 | 15.1 | 28.3 | 1.7 | 4.4 | 3 | 3.5 |  |  |  | 3 |
| Deviation | 3.93 | 5.33 | 9.5 | 0.9 | −1.5 | −1 | −1.5 |  |  |  | 1.5 |
| Significance | * | ** | * | + | * |  |  |  |  |  |  |
| # Obs | 31 | 8 | 4 | 5 | 11 | 2 | 2 |  |  |  | 1 |
| Years | 2 | 2 | 1 | 1 | 2 | 1 | 1 |  |  |  | 1 |
| Win Percent | 77 | 0 | 0 | 0 | 82 | 100 | 100 |  |  |  | 0 |
| Test Mean | 53.4 | 17.6 | 34.5 | 3.3 | 3.9 | 3.3 | 3.2 |  |  |  | 3.4 |
| A1026138 | 56.7 | 21 | 37.8 | 2.1 | 2.9 | 2 | 2 | 40.8 | 21 | 2,935.5 | 4.5 |
| CSR2252N | 52.5 | 17.9 | 34 | 2.4 | 3.6 | 3.5 | 3 | 39.5 | 22.8 | 3,044 | 2.8 |
| Deviation | 4.24 | 3.04 | 3.75 | −0.28 | −0.73 | −1.5 | −1 | 1.22 | −1.77 | −108.5 | 1.67 |
| Significance | ** | ** |  |  |  |  |  |  | ** |  |  |
| # Obs | 36 | 10 | 4 | 8 | 11 | 2 | 2 | 2 | 2 | 2 | 1 |

TABLE 2-continued

Exemplary Agronomic Traits of A1026138 vs Selected and Competing Varieties

| Entries Compared | YLD_BE | MAT | PHT | LDG | PSC | EMR | SDV | PRO | OIL | SWT | IDC |
|---|---|---|---|---|---|---|---|---|---|---|---|
| Years | 2 | 2 | 1 | 1 | 2 | 1 | 1 | 1 | 1 | 1 | 1 |
| Win Percent | 78 | 10 | 0 | 50 | 86 | 100 | 100 | 50 | 0 | 50 | 0 |
| Test Mean | 53.2 | 18.5 | 34.4 | 2.8 | 3.8 | 3.3 | 3.2 | 41.6 | 21.4 | 2,898.8 | 3.4 |
| A1026138 | 56.7 | 20.1 | 37.8 | 2.6 | 2.9 | 2 | 2 | | | | 4.5 |
| CSR2522N | 51.6 | 18.8 | 32.4 | 3.1 | 4.3 | 2.3 | 3 | | | | 2.9 |
| Deviation | 5.07 | 1.33 | 5.38 | −0.45 | −1.36 | −0.25 | −1 | | | | 1.58 |
| Significance | ** | + | + | | + | ** | ** | | | | |
| # Obs | 34 | 6 | 4 | 5 | 9 | 2 | 2 | | | | 1 |
| Years | 2 | 2 | 1 | 1 | 1 | 1 | 1 | | | | 1 |
| Win Percent | 85 | 20 | 0 | 67 | 88 | 100 | 100 | | | | 0 |
| Test Mean | 53.1 | 18.7 | 34.7 | 3.3 | 4 | 3.3 | 3.1 | | | | 3.5 |
| A1026138 | 56.6 | 20.6 | 36.6 | 2.6 | 3 | 2 | 2 | 39.5 | 20.7 | | 4.5 |
| CSRV2409N | 49.6 | 20 | 33 | 3.4 | 4.1 | 5.3 | 3.5 | 39.4 | 21.1 | | 3.8 |
| Deviation | 6.97 | 0.64 | 3.6 | −0.8 | −1.1 | −3.25 | −1.5 | 0.1 | −0.4 | | 0.67 |
| Significance | ** | | * | + | * | | | | | | |
| # Obs | 30 | 7 | 5 | 5 | 10 | 2 | 2 | 1 | 1 | | 1 |
| Years | 2 | 2 | 2 | 1 | 2 | 1 | 1 | 1 | 1 | 1 | 1 |
| Win Percent | 87 | 33 | 0 | 100 | 100 | 100 | 100 | 100 | 0 | 0 | 0 |
| Test Mean | 53.6 | 18.6 | 33.9 | 3.4 | 4 | 3.3 | 3.2 | 40.5 | 20.7 | | 3.4 |
| A1026138 | 56.4 | 19.5 | 36.7 | 2 | 3.1 | 2 | 2 | 40.3 | 21 | 3,016.5 | 4.5 |
| DEI1230RR2N | 55.7 | 17.9 | 37.8 | 3.1 | 4 | 3.8 | 3 | 41.8 | 21.6 | 2,535.5 | 2.8 |
| Deviation | 0.67 | 1.58 | −1.17 | −1.09 | −0.92 | −1.75 | −1 | −1.52 | −0.6 | 481 | 1.67 |
| Significance | | ** | | * | ** | | ** | * | | * | |
| # Obs | 35 | 13 | 6 | 11 | 12 | 2 | 2 | 5 | 5 | 4 | 1 |
| Years | 2 | 2 | 2 | 1 | 2 | 1 | 1 | 2 | 2 | 1 | 1 |
| Win Percent | 63 | 0 | 80 | 89 | 100 | 100 | 100 | 0 | 0 | 100 | 0 |
| Test Mean | 53.4 | 17.2 | 35.8 | 2.8 | 4.1 | 3.5 | 3.1 | 41.1 | 21.4 | 2,873.2 | 3.5 |
| A1026138 | 56.4 | 19.9 | 37.6 | 2 | 3.1 | 2 | 2 | 40.5 | 21 | 3,016.5 | 4.5 |
| PS 2290 NR2 | 52.6 | 19.1 | 41.3 | 2.3 | 3.3 | 3 | 2.5 | 41.3 | 20.5 | 3,085 | 3.5 |
| Deviation | 3.79 | 0.75 | −3.7 | −0.3 | −0.25 | −1 | −0.5 | −0.8 | 0.55 | −68.5 | 1 |
| Significance | ** | | + | | | | | | + | | |
| # Obs | 37 | 14 | 5 | 11 | 12 | 2 | 2 | 4 | 4 | 4 | 1 |
| Years | 2 | 2 | 1 | 1 | 2 | 1 | 1 | 1 | 1 | 1 | 1 |
| Win Percent | 73 | 18 | 80 | 67 | 67 | 100 | 100 | 0 | 100 | 33 | 0 |
| Test Mean | 53.2 | 17.8 | 36.2 | 2.8 | 4.1 | 3.5 | 3.1 | 41.3 | 21.5 | 2,873.2 | 3.5 |
| A1026138 | 56.1 | 20.4 | 37.8 | 2.6 | 2.9 | 2 | 2 | | | | 4.5 |
| DKB22-52 | 50.3 | 16.7 | 30 | 3.1 | 4.6 | 2.8 | 4.5 | | | | 2.8 |
| Deviation | 5.84 | 3.72 | 7.75 | −0.49 | −1.74 | −0.75 | −2.5 | | | | 1.67 |
| Significance | ** | ** | * | | ** | | | | | | |
| # Obs | 32 | 8 | 4 | 5 | 11 | 2 | 2 | | | | 1 |
| Years | 2 | 2 | 1 | 1 | 2 | 1 | 1 | | | | 1 |
| Win Percent | 88 | 12 | 0 | 75 | 91 | 100 | 100 | | | | 0 |
| Test Mean | 53.2 | 17.8 | 34.7 | 3.4 | 3.9 | 3.1 | 3.2 | | | | 3.4 |
| A1026138 | 56.7 | 20.9 | 37.8 | 2.6 | 3 | 2 | 2 | | | | 4.5 |
| DKB25-51 | 49.7 | 20.3 | 32.6 | 2.7 | 4.3 | 2.9 | 3.3 | | | | 3.8 |
| Deviation | 6.94 | 0.59 | 5.12 | −0.1 | −1.33 | −0.88 | −1.25 | | | | 0.75 |
| Significance | ** | | + | | * | | | | | | |
| # Obs | 34 | 8 | 4 | 5 | 10 | 2 | 2 | | | | 1 |
| Years | 2 | 2 | 1 | 1 | 2 | 1 | 1 | | | | 1 |
| Win Percent | 88 | 50 | 0 | 75 | 89 | 100 | 100 | | | | 0 |
| Test Mean | 53 | 19.7 | 34.7 | 3.3 | 4 | 3.3 | 3.1 | | | | 3.5 |
| A1026138 | 56.6 | 20.3 | 36.6 | 2.3 | 3.1 | 2 | 2 | 39.4 | 21 | | 4.5 |
| DKB26-53 | 54.5 | 22 | 35.3 | 3.3 | 4 | 2.6 | 3.3 | 39.6 | 21.4 | | 3.8 |
| Deviation | 2.08 | −1.77 | 1.26 | −1.01 | −0.89 | −0.57 | −1.25 | −0.23 | −0.43 | | 0.75 |
| Significance | + | ** | | + | * | | | | | | |
| # Obs | 35 | 11 | 5 | 6 | 12 | 2 | 2 | 2 | 2 | | 1 |
| Years | 2 | 2 | 2 | 1 | 2 | 1 | 1 | 1 | 1 | | 1 |
| Win Percent | 74 | 100 | 20 | 100 | 90 | 100 | 100 | 0 | 0 | | 0 |
| Test Mean | 52.5 | 19.1 | 34.4 | 3 | 4.1 | 2.8 | 3.1 | 40.1 | 21.2 | | 3.5 |
| A1026138 | 56.3 | 19.9 | 37.8 | 2.6 | 2.9 | 2 | 2 | | | | 4.5 |
| 30-61RY | 55.7 | 14.7 | 32.9 | 3.5 | 3.4 | 3.3 | 6 | | | | 3 |
| Deviation | 0.58 | 5.21 | 4.88 | −0.9 | −0.5 | −1.25 | −4 | | | | 1.5 |
| Significance | | ** | + | | | | | | | | |
| # Obs | 31 | 7 | 4 | 5 | 11 | 2 | 2 | | | | 1 |
| Years | 2 | 2 | 1 | 1 | 2 | 1 | 1 | | | | 1 |
| Win Percent | 55 | 0 | 0 | 100 | 62 | 50 | 100 | | | | 0 |
| Test Mean | 53.1 | 16.8 | 34.5 | 3.3 | 3.9 | 3.3 | 3.2 | | | | 3.4 |
| A1026138 | 56.5 | 19.9 | 37.6 | 2 | 3.1 | 2 | 2 | 40.5 | 21 | 3,016.5 | 4.5 |
| 31-10RY | 55.2 | 16.6 | 35.4 | 3.3 | 4.7 | 2.4 | 3.1 | 40.7 | 21.5 | 2,995.6 | 3.6 |
| Deviation | 1.37 | 3.22 | 2.17 | −1.26 | −1.65 | −0.42 | −1.08 | −0.2 | −0.5 | 20.88 | 0.89 |
| Significance | | ** | * | ** | ** | | | | * | | |
| # Obs | 38 | 14 | 5 | 11 | 12 | 2 | 2 | 4 | 4 | 4 | 1 |
| Years | 2 | 2 | 1 | 1 | 2 | 1 | 1 | 1 | 1 | 1 | 1 |
| Win Percent | 61 | 0 | 0 | 100 | 83 | 100 | 100 | 75 | 0 | 50 | 0 |
| Test Mean | 53.4 | 18.7 | 35.3 | 2.7 | 4.1 | 3.2 | 3.4 | 41.4 | 21.4 | 2,885.6 | 3.4 |
| A1026138 | 56.5 | 19.9 | 37.6 | 2 | 3.1 | 2 | 2 | 40.5 | 21 | 3,016.5 | 4.5 |

TABLE 2-continued

Exemplary Agronomic Traits of A1026138 vs Selected and Competing Varieties

| Entries Compared | YLD_BE | MAT | PHT | LDG | PSC | EMR | SDV | PRO | OIL | SWT | IDC |
|---|---|---|---|---|---|---|---|---|---|---|---|
| 31-11RY | 54 | 19.6 | 34.9 | 2 | 3.7 | 2.9 | 4 | 40 | 21.9 | 3,186.4 | 3.1 |
| Deviation | 2.53 | 0.29 | 2.74 | −0.01 | −0.58 | −0.87 | −2 | 0.5 | −0.88 | −169.88 | 1.39 |
| Significance | ** | | + | | + | | | * | | | |
| # Obs | 38 | 14 | 5 | 11 | 12 | 2 | 2 | 4 | 4 | 4 | 1 |
| Years | 2 | 2 | 1 | 1 | 2 | 1 | 1 | 1 | 1 | 1 | 1 |
| Win Percent | 74 | 50 | 0 | 67 | 82 | 100 | 100 | 50 | 0 | 33 | 0 |
| Test Mean | 52.8 | 19.3 | 35.4 | 2.6 | 4.1 | 2.8 | 3.1 | 41.4 | 21.4 | 2,889.1 | 3.5 |
| A1026138 | 56.5 | 20.1 | 36.7 | 2 | 3.1 | 2 | 2 | 40.2 | 21 | 3,016.5 | 4.5 |
| 31-52R | 51.9 | 17.7 | 34.9 | 2.3 | 3.3 | 2.9 | 2.5 | 41.6 | 21.4 | 2,931.9 | 4.1 |
| Deviation | 4.61 | 2.4 | 1.81 | −0.29 | −0.25 | −0.88 | −0.5 | −1.4 | −0.36 | 84.62 | 0.42 |
| Significance | ** | ** | | | | | ** | * | ** | | |
| # Obs | 39 | 15 | 6 | 11 | 12 | 2 | 2 | 6 | 6 | 4 | 1 |
| Years | 2 | 2 | 2 | 1 | 2 | 1 | 1 | 2 | 2 | 1 | 1 |
| Win Percent | 92 | 0 | 25 | 83 | 56 | 100 | 100 | 17 | 0 | 67 | 0 |
| Test Mean | 52.9 | 18.1 | 34.6 | 2.7 | 4 | 3.3 | 3.2 | 40.9 | 21.4 | 2,889.1 | 3.4 |
| A1026138 | 56.6 | 20.6 | 37.8 | 2.6 | 3.2 | 2 | 2 | | | | 4.5 |
| BPR15987RR | 56.7 | 20.6 | 33.1 | 2.9 | 4.5 | 3.3 | 2.5 | | | | 3.8 |
| Deviation | −0.16 | 0.07 | 4.62 | −0.3 | −1.31 | −1.25 | −0.5 | | | | 0.67 |
| Significance | | | + | | ** | | | | | | |
| # Obs | 30 | 7 | 4 | 5 | 9 | 2 | 2 | | | | 1 |
| Years | 2 | 2 | 1 | 1 | 2 | 1 | 1 | | | | 1 |
| Win Percent | 50 | 67 | 0 | 75 | 89 | 100 | 100 | | | | 0 |
| Test Mean | 53.6 | 18.4 | 34.5 | 3.4 | 4 | 3.3 | 3.2 | | | | 3.4 |
| A1026138 | 56.2 | 19.1 | 37.6 | 2 | 3.1 | 2 | 2 | 40.5 | 21 | 3,016.5 | 4.5 |
| RB2101R2N | 55.6 | 15.4 | 35 | 2.2 | 3.1 | 1.8 | 3.5 | 41.5 | 21.1 | 3,186 | 3.7 |
| Deviation | 0.63 | 3.71 | 2.6 | −0.18 | −0.05 | 0.25 | −1.5 | −0.98 | −0.05 | −169.5 | 0.83 |
| Significance | | ** | + | | | | | * | | | |
| # Obs | 34 | 12 | 5 | 11 | 11 | 2 | 2 | 4 | 4 | 4 | 1 |
| Years | 2 | 1 | 1 | 1 | 1 | 1 | 1 | 1 | 1 | 1 | 1 |
| Win Percent | 62 | 0 | 0 | 67 | 50 | 0 | 100 | 0 | 50 | 25 | 0 |
| Test Mean | 53.2 | 16.7 | 36.2 | 2.8 | 4.1 | 3.5 | 3.1 | 41.3 | 21.5 | 2,873.2 | 3.5 |
| A1026138 | 56.6 | 20.6 | 37.8 | 2.6 | 3 | 2 | 2 | | | | 4.5 |
| CB2391R2N | 55.5 | 18.5 | 34.1 | 2.3 | 3.3 | 3.5 | 2.5 | | | | 2.5 |
| Deviation | 1.05 | 2.14 | 3.62 | 0.3 | −0.3 | −1.5 | −0.5 | | | | 2 |
| Significance | | ** | + | | | | | | | | |
| # Obs | 30 | 7 | 4 | 5 | 10 | 2 | 2 | | | | 1 |
| Years | 2 | 2 | 1 | 1 | 2 | 1 | 1 | | | | 1 |
| Win Percent | 63 | 0 | 0 | 50 | 71 | 100 | 100 | | | | 0 |
| Test Mean | 53.7 | 18.6 | 34.5 | 3.4 | 4 | 3.3 | 3.2 | | | | 3.4 |
| A1026138 | 56.7 | 19.1 | 37.6 | 2.2 | 2.9 | 2 | 2 | 40.2 | 21.2 | 3,247 | 4.5 |
| CB2491R2 | 57.9 | 18.4 | 33.5 | 2.2 | 3.4 | 1.8 | 3 | 40.7 | 21.5 | 2,841 | 3.5 |
| Deviation | −1.23 | 0.7 | 4.1 | 0.02 | −0.46 | 0.25 | −1 | −0.45 | −0.35 | 406 | 1 |
| Significance | | | + | | | | ** | | | | |
| # Obs | 30 | 11 | 5 | 9 | 9 | 2 | 2 | 1 | 1 | 1 | 1 |
| Years | 1 | 1 | 1 | 1 | 1 | 1 | 1 | 1 | 1 | 1 | 1 |
| Win Percent | 50 | 50 | 20 | 50 | 75 | 0 | 100 | 0 | 0 | 100 | 0 |
| Test Mean | 53.8 | 17.7 | 34.9 | 2.9 | 4.1 | 3.3 | 3.2 | 41.5 | 21.2 | 2,851.1 | 3.4 |
| A1026138 | 56.6 | 19.5 | 37.6 | 2 | 3.1 | 2 | 2 | 40.3 | 21 | 3,016.5 | 4.5 |
| EXP221N | 56.1 | 15.9 | 36.5 | 3.1 | 4.2 | 3.3 | 3 | 41.6 | 21.2 | 2,673.8 | 2.7 |
| Deviation | 0.43 | 3.58 | 1.1 | −1.14 | −1.14 | −1.25 | −1 | −1.3 | −0.22 | 342.75 | 1.83 |
| Significance | | ** | | ** | ** | ** | ** | * | | + | |
| # Obs | 37 | 13 | 5 | 11 | 11 | 2 | 2 | 5 | 5 | 4 | 1 |
| Years | 2 | 2 | 1 | 1 | 1 | 1 | 1 | 2 | 2 | 1 | 1 |
| Win Percent | 59 | 0 | 50 | 91 | 91 | 100 | 100 | 0 | 20 | 100 | 0 |
| Test Mean | 53.5 | 17.3 | 36.2 | 2.8 | 4.1 | 3.5 | 3.1 | 41.1 | 21.4 | 2,873.2 | 3.5 |
| A1026138 | 56.6 | 20.6 | 37.8 | 2.6 | 3 | 2 | 2 | | | | 4.5 |
| 92M11 | 51.1 | 16.2 | 33.9 | 3.6 | 5.1 | 3 | 3.5 | | | | 3.7 |
| Deviation | 5.45 | 4.41 | 3.88 | −1 | −2.12 | −1 | −1.5 | | | | 0.83 |
| Significance | ** | ** | | | ** | | | | | | |
| # Obs | 30 | 7 | 4 | 5 | 10 | 2 | 2 | | | | 1 |
| Years | 2 | 2 | 1 | 1 | 2 | 1 | 1 | | | | 1 |
| Win Percent | 83 | 0 | 0 | 75 | 100 | 100 | 100 | | | | 0 |
| Test Mean | 53.7 | 18.3 | 34.5 | 3.4 | 4 | 3.3 | 3.2 | | | | 3.4 |
| A1026138 | 56.3 | 19.6 | 37.6 | 2.4 | 3 | 2 | 2 | | | | 4.5 |
| 92M40 | 49.4 | 17.9 | 31.6 | 2.1 | 4.3 | 2.5 | 2.5 | | | | 4.2 |
| Deviation | 6.89 | 1.65 | 6 | 0.29 | −1.3 | −0.5 | −0.5 | | | | 0.33 |
| Significance | ** | * | ** | | * | ** | | | | | |
| # Obs | 32 | 10 | 5 | 7 | 10 | 2 | 2 | | | | 1 |
| Years | 2 | 2 | 1 | 1 | 2 | 1 | 1 | | | | 1 |
| Win Percent | 91 | 22 | 0 | 25 | 89 | 100 | 50 | | | | 0 |
| Test Mean | 53.4 | 18.1 | 34.8 | 3 | 4 | 3.3 | 3.2 | | | | 3.4 |
| A1026138 | 56.8 | 20.2 | 37.8 | 2.3 | 2.9 | 2 | 2 | 40.5 | 21.4 | 3,030 | 4.5 |
| 92Y10 | 52.3 | 15.2 | 30.1 | 2.9 | 4.8 | 4.5 | 3.5 | 41.8 | 21.1 | 2,841 | 3.3 |
| Deviation | 4.45 | 5 | 7.63 | −0.57 | −1.83 | −2.5 | −1.5 | −1.3 | 0.3 | 189 | 1.17 |
| Significance | ** | ** | * | | ** | | | | | | |
| # Obs | 29 | 7 | 4 | 7 | 9 | 2 | 2 | 1 | 1 | 1 | 1 |

TABLE 2-continued

Exemplary Agronomic Traits of A1026138 vs Selected and Competing Varieties

| Entries Compared | YLD_BE | MAT | PHT | LDG | PSC | EMR | SDV | PRO | OIL | SWT | IDC |
|---|---|---|---|---|---|---|---|---|---|---|---|
| Years | 1 | 1 | 1 | 1 | 1 | 1 | 1 | 1 | 1 | 1 | 1 |
| Win Percent | 79 | 0 | 0 | 67 | 100 | 100 | 100 | 0 | 100 | 100 | 0 |
| Test Mean | 54 | 18.1 | 34.5 | 3 | 4 | 3.3 | 3.2 | 42.3 | 21.1 | 2,844.4 | 3.4 |
| A1026138 | 56.1 | 20.6 | 37.8 | 2.6 | 3.2 | 2 | 2 | 40.5 | 21 | 3,016.5 | 4.5 |
| 92Y20 | 52.8 | 16.1 | 32.7 | 3.7 | 4.7 | 3.8 | 2.8 | 38.8 | 23.3 | 2,982 | 4.3 |
| Deviation | 3.34 | 4.57 | 5.06 | −1.1 | −1.5 | −1.75 | −0.75 | 1.7 | −2.29 | 34.5 | 0.17 |
| Significance | ** | ** | ** |  | ** |  |  | * | ** |  |  |
| # Obs | 32 | 7 | 4 | 5 | 11 | 2 | 2 | 4 | 4 | 4 | 1 |
| Years | 2 | 2 | 1 | 1 | 2 | 1 | 1 | 1 | 1 | 1 | 1 |
| Win Percent | 81 | 0 | 0 | 100 | 100 | 100 | 100 | 100 | 0 | 50 | 0 |
| Test Mean | 53.3 | 18.6 | 34.3 | 3.4 | 4.1 | 3.4 | 3.2 | 41.4 | 21.4 | 2,855.4 | 3.6 |
| A1026138 | 56.7 | 20.2 | 37.6 | 2.3 | 3 | 2 | 2 | 40.2 | 21.2 | 3,247 | 4.5 |
| 92Y30 | 53.4 | 18.3 | 32.2 | 2.4 | 4.1 | 4.5 | 4 | 40.8 | 22.6 | 3,030 | 3.7 |
| Deviation | 3.29 | 1.92 | 5.4 | −0.08 | −1.15 | −2.5 | −2 | −0.6 | −1.4 | 217 | 0.83 |
| Significance | * | * | * |  | * |  | ** |  |  |  |  |
| # Obs | 32 | 10 | 5 | 6 | 10 | 2 | 2 | 1 | 1 | 1 | 1 |
| Years | 2 | 2 | 1 | 1 | 2 | 1 | 1 | 1 | 1 | 1 | 1 |
| Win Percent | 78 | 12 | 0 | 67 | 88 | 100 | 100 | 0 | 0 | 100 | 0 |
| Test Mean | 53.7 | 18.4 | 35 | 3.1 | 3.9 | 3.3 | 3.2 | 41.4 | 21.3 | 2,839.3 | 3.4 |
| A1026138 | 56.6 | 19.1 | 37.6 | 2.3 | 2.9 | 2 | 2 | 40.2 | 21.2 | 3,247 | 4.5 |
| 92Y31 | 54.2 | 15.8 | 33.3 | 2.3 | 3.8 | 3.3 | 2 | 42.2 | 21.4 | 2,392 | 2.5 |
| Deviation | 2.49 | 3.38 | 4.3 | 0 | −0.83 | −1.25 | 0 | −2 | −0.2 | 855 | 2 |
| Significance |  | ** | ** |  |  |  |  |  |  |  |  |
| # Obs | 27 | 8 | 5 | 6 | 9 | 2 | 2 | 1 | 1 | 1 | 1 |
| Years | 1 | 1 | 1 | 1 | 1 | 1 | 1 | 1 | 1 | 1 | 1 |
| Win Percent | 70 | 0 | 0 | 60 | 71 | 100 | 50 | 0 | 0 | 100 | 0 |
| Test Mean | 53.9 | 17.1 | 35 | 3.1 | 4 | 3.3 | 3.2 | 41.4 | 21.3 | 2,839.3 | 3.4 |
| A1026138 | 56.6 | 20.6 | 37.8 | 2.6 | 3 | 2 | 2 |  |  |  | 4.5 |
| S21-N6 | 53.3 | 17.3 | 31.8 | 2.5 | 5.1 | 3.8 | 2 |  |  |  | 3.3 |
| Deviation | 3.22 | 3.32 | 6 | 0.1 | −2.18 | −1.75 | 0 |  |  |  | 1.17 |
| Significance | * | ** | * |  | ** |  |  |  |  |  |  |
| # Obs | 30 | 7 | 4 | 5 | 10 | 2 | 2 |  |  |  | 1 |
| Years | 2 | 2 | 1 | 1 | 2 | 1 | 1 |  |  |  | 1 |
| Win Percent | 77 | 0 | 0 | 50 | 100 | 100 | — |  |  |  | 0 |
| Test Mean | 53.6 | 18.3 | 34.5 | 3.4 | 4 | 3.3 | 3.2 |  |  |  | 3.4 |
| A1026138 | 56.6 | 20.6 | 37.8 | 2.6 | 3 | 2 | 2 |  |  |  | 4.5 |
| S24-J1 | 52.6 | 17.9 | 29.8 | 3.6 | 4.5 | 4.3 | 3.5 |  |  |  | 3.5 |
| Deviation | 3.96 | 2.71 | 8 | −1 | −1.55 | −2.25 | −1.5 |  |  |  | 1 |
| Significance | ** | + | * | * | ** |  |  |  |  |  |  |
| # Obs | 30 | 7 | 4 | 5 | 10 | 2 | 2 |  |  |  | 1 |
| Years | 2 | 2 | 1 | 1 | 2 | 1 | 1 |  |  |  | 1 |
| Win Percent | 90 | 0 | 0 | 100 | 100 | 100 | 100 |  |  |  | 0 |
| Test Mean | 53.7 | 18.5 | 34.5 | 3.4 | 4 | 3.3 | 3.2 |  |  |  | 3.4 |

\*\*, \*, + Significant at P < 0.01, 0.05, or 0.10, respectively

I. Breeding Soybean Variety A1026138

One aspect of the current invention concerns methods for crossing the soybean variety A1026138 with itself or a second plant and the seeds and plants produced by such methods. These methods can be used for propagation of the soybean variety A1026138, or can be used to produce hybrid soybean seeds and the plants grown therefrom. Hybrid soybean plants can be used by farmers in the commercial production of soy products or may be advanced in certain breeding protocols for the production of novel soybean varieties. A hybrid plant can also be used as a recurrent parent at any given stage in a backcrossing protocol during the production of a single locus conversion of the soybean variety A1026138.

Soybean variety A1026138 is well suited to the development of new varieties based on the elite nature of the genetic background of the variety. In selecting a second plant to cross with A1026138 for the purpose of developing novel soybean varieties, it will typically be desired to choose those plants which either themselves exhibit one or more selected desirable characteristics or which exhibit the desired characteristic(s) when in hybrid combination. Examples of potentially desired characteristics include seed yield, lodging resistance, emergence, seedling vigor, disease tolerance, maturity, plant height, high oil content, high protein content and shattering resistance.

Choice of breeding or selection methods depends on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection and backcrossing.

The complexity of inheritance influences choice of the breeding method. Backcross breeding is used to transfer one or a few favorable genes for a highly heritable trait into a desirable variety. This approach has been used extensively for breeding disease-resistant varieties (Bowers et al., *Crop Sci.*, 32(1):67-72, 1992; Nickell and Bernard, *Crop Sci.*, 32(3): 835, 1992). Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input (e.g., per year, per dollar expended, etc.).

Promising advanced breeding lines are thoroughly tested and compared to appropriate standards in environments representative of the commercial target area(s) for generally three or more years. The best lines are candidates for new commercial varieties. Those still deficient in a few traits may be used as parents to produce new populations for further selection.

These processes, which lead to the final step of marketing and distribution, may take as much as eight to 12 years from the time the first cross is made. Therefore, development of new varieties is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to one or more widely grown standard varieties. Single observations are generally inconclusive, while replicated observations provide a better estimate of genetic worth.

The goal of plant breeding is to develop new, unique and superior soybean varieties and hybrids. The breeder initially selects and crosses two or more parental lines, followed by repeated selfing and selection, producing many new genetic combinations. Each year, the plant breeder selects the germplasm to advance to the next generation. This germplasm is grown under unique and different geographical, climatic and soil conditions, and further selections are then made, during and at the end of the growing season. The varieties which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same variety twice by using the exact same original parents and the same selection techniques. This unpredictability results in the expenditure of large amounts of research monies to develop superior new soybean varieties.

Pedigree breeding and recurrent selection breeding methods are used to develop varieties from breeding populations. Breeding programs combine desirable traits from two or more varieties or various broad-based sources into breeding pools from which varieties are developed by selfing and selection of desired phenotypes. The new varieties are evaluated to determine which have commercial potential.

Pedigree breeding is commonly used for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population (or later depending upon the breeder's objectives); then, beginning in the $F_3$, the best individuals in the best families can be selected. Replicated testing of families can begin in the $F_3$ or $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genetic loci for simply inherited, highly heritable traits into a desirable homozygous variety which is the recurrent parent. The source of the trait to be transferred is called the donor or nonrecurrent parent. The resulting plant is expected to have the attributes of the recurrent parent (i.e., variety) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (i.e., variety) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. This procedure is also referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, "Principles of plant breeding," John Wiley & Sons, NY, University of California, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, In: *Soybeans: Improvement, Production and Uses,"* 2d Ed., *Manograph* 16:249, 1987; Fehr, "Principles of variety development," Theory and Technique (Vol 1) and Crop Species Soybean (Vol 2), Iowa State Univ., Macmillian Pub. Co., NY, 360-376, 1987; Poehlman and Sleper, "Breeding Field Crops" Iowa State University Press, Ames, 1995; Sprague and Dudley, eds., *Corn and Improvement,* 5th ed., 2006).

Proper testing should detect any major faults and establish the level of superiority or improvement over current varieties. In addition to showing superior performance, there must be a demand for a new variety that is compatible with industry standards or which creates a new market. The introduction of a new variety will incur additional costs to the seed producer, the grower, processor and consumer; for special advertising and marketing, altered seed and commercial production practices, and new product utilization. The testing preceding release of a new variety should take into consideration research and development costs as well as technical superiority of the final variety. For seed-propagated varieties, it must be feasible to produce seed easily and economically.

Any time the soybean variety A1026138 is crossed with another, different, variety, first generation ($F_1$) soybean progeny are produced. The hybrid progeny are produced regardless of characteristics of the two varieties produced. As such, an $F_1$ hybrid soybean plant may be produced by crossing A1026138 with any second soybean plant. The second soybean plant may be genetically homogeneous (e.g., inbred) or may itself be a hybrid. Therefore, any $F_1$ hybrid soybean plant produced by crossing soybean variety A1026138 with a second soybean plant is a part of the present invention.

Soybean plants (*Glycine max* L.) can be crossed by either natural or mechanical techniques (see, e.g., Fehr, "Soybean," In: *Hybridization of Crop Plants*, Fehr and Hadley (eds), *Am. Soc. Agron.* and *Crop Sci. Soc. Am.*, Madison, Wis., 590-599, 1980). Natural pollination occurs in soybeans either by self pollination or natural cross pollination, which typically is aided by pollinating organisms. In either natural or artificial crosses, flowering and flowering time are an important consideration. Soybean is a short-day plant, but there is considerable genetic variation for sensitivity to photoperiod (Hamner, "*Glycine max* (L.) Merrill," In: *The Induction of Flowering: Some Case Histories*, Evans (ed), Cornell Univ. Press, Ithaca, N.Y., 62-89, 1969; Criswell and Hume, *Crop Sci.*, 12:657-660, 1972). The critical day length for flowering ranges from about 13 h for genotypes adapted to tropical latitudes to 24 h for photoperiod-insensitive genotypes grown at higher latitudes (Shibles et al., "Soybean," In: *Crop Physiology, Some Case Histories*, Evans (ed), Cambridge Univ. Press, Cambridge, England, 51-189, 1975). Soybeans seem to be insensitive to day length for 9 days after emergence. Photoperiods shorter than the critical day length are required for 7 to 26 days to complete flower induction (Borthwick and Parker, *Bot. Gaz.*, 100:374-387, 1938; Shanmugasundaram and Tsou, *Crop Sci.*, 18:598-601, 1978).

Sensitivity to day length is an important consideration when genotypes are grown outside of their area of adaptation. When genotypes adapted to tropical latitudes are grown in the field at higher latitudes, they may not mature before frost occurs. Plants can be induced to flower and mature earlier by creating artificially short days or by grafting (Fehr, "Soybean," In: *Hybridization of Crop Plants*, Fehr and Hadley (eds), *Am. Soc. Agron.* and *Crop Sci. Soc. Am.*, Madison, Wis., 590-599, 1980). Soybeans frequently are grown in winter nurseries located at sea level in tropical latitudes where day lengths are much shorter than their critical photoperiod. The short day lengths and warm temperatures encourage early flowering and seed maturation, and genotypes can produce a seed crop in 90 days or fewer after planting. Early flowering is useful for generation advance when only a few self-pollinated seeds per plant are needed, but not for artificial hybridization because the flowers self-pollinate before they are large enough to manipulate for hybridization. Artificial lighting can be used to extend the natural day length to about 14.5 h to obtain flowers suitable for hybridization and to increase yields of self-pollinated seed.

The effect of a short photoperiod on flowering and seed yield can be partly offset by altitude, probably due to the effects of cool temperature (Major et al., *Crop Sci.*, 15:174-179, 1975). At tropical latitudes, varieties adapted to the northern U.S. perform more like those adapted to the southern U.S. at high altitudes than they do at sea level.

The light level required to delay flowering is dependent on the quality of light emitted from the source and the genotype being grown. Blue light with a wavelength of about 480 nm requires more than 30 times the energy to inhibit flowering as red light with a wavelength of about 640 nm (Parker et al., *Bot. Gaz.*, 108:1-26, 1946).

Temperature can also play a significant role in the flowering and development of soybean (Major et al., *Crop Sci.*, 15:174-179, 1975). It can influence the time of flowering and suitability of flowers for hybridization. Temperatures below 21° C. or above 32° C. can reduce floral initiation or seed set (Hamner, "*Glycine max* (L.) Merrill," In: *The Induction of Flowering: Some Case Histories*, Evans (ed), Cornell Univ. Press, Ithaca, N.Y., 62-89, 1969; van Schaik and Probst, *Agron. J.*, 50:192-197, 1958). Artificial hybridization is most successful between 26° C. and 32° C. because cooler temperatures reduce pollen shed and result in flowers that self-pollinate before they are large enough to manipulate. Warmer temperatures frequently are associated with increased flower abortion caused by moisture stress; however, successful crosses are possible at about 35° C. if soil moisture is adequate.

Soybeans have been classified as indeterminate, semi-determinate, and determinate based on the abruptness of stem termination after flowering begins (Bernard and Weiss, "Qualitative genetics," In: *Soybeans: Improvement, Production, and Uses*, Caldwell (ed), *Am. Soc. of Agron.*, Madison, Wis., 117-154, 1973). When grown at their latitude of adaptation, indeterminate genotypes flower when about one-half of the nodes on the main stem have developed. They have short racemes with few flowers, and their terminal node has only a few flowers. Semi-determinate genotypes also flower when about one-half of the nodes on the main stem have developed, but node development and flowering on the main stem stops more abruptly than on indeterminate genotypes. Their racemes are short and have few flowers, except for the terminal one, which may have several times more flowers than those lower on the plant. Determinate varieties begin flowering when all or most of the nodes on the main stem have developed. They usually have elongated racemes that may be several centimeters in length and may have a large number of flowers. Stem termination and flowering habit are reported to be controlled by two major genes (Bernard and Weiss, "Qualitative genetics," In: *Soybeans: Improvement, Production, and Uses*, Caldwell (ed), *Am. Soc. of Agron.*, Madison, Wis., 117-154, 1973).

Soybean flowers typically are self-pollinated on the day the corolla opens. The amount of natural crossing, which is typically associated with insect vectors such as honeybees, is approximately 1% for adjacent plants within a row and 0.5% between plants in adjacent rows (Boerma and Moradshahi, *Crop Sci.*, 15:858-861, 1975). The structure of soybean flowers is similar to that of other legume species and consists of a calyx with five sepals, a corolla with five petals, 10 stamens, and a pistil (Carlson, "Morphology", In: *Soybeans: Improvement, Production, and Uses*, Caldwell (ed), *Am. Soc. of Agron.*, Madison, Wis., 17-95, 1973). The calyx encloses the corolla until the day before anthesis. The corolla emerges and unfolds to expose a standard, two wing petals, and two keel petals. An open flower is about 7 mm long from the base of the calyx to the tip of the standard and 6 mm wide across the standard. The pistil consists of a single ovary that contains one to five ovules, a style that curves toward the standard, and a club-shaped stigma. The stigma is receptive to pollen about 1 day before anthesis and remains receptive for 2 days after anthesis, if the flower petals are not removed. Filaments of nine stamens are fused, and the one nearest the standard is free. The stamens form a ring below the stigma until about 1 day before anthesis, then their filaments begin to elongate rapidly and elevate the anthers around the stigma. The anthers dehisce on the day of anthesis, pollen grains fall on the stigma, and within 10 h the pollen tubes reach the ovary and fertilization is completed (Johnson and Bernard, "Soybean genetics and breeding," In: *The Soybean*, Norman (ed), Academic Press, NY, 1-73, 1963).

Self-pollination occurs naturally in soybean with no manipulation of the flowers. For the crossing of two soybean plants, it is often beneficial, although not required, to utilize artificial hybridization. In artificial hybridization, the flower used as a female in a cross is manually cross pollinated prior to maturation of pollen from the flower, thereby preventing self fertilization, or alternatively, the male parts of the flower are emasculated using a technique known in the art. Techniques for emasculating the male parts of a soybean flower include, for example, physical removal of the male parts, use of a genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed with forceps. Special care is required to remove immature buds that are hidden under the stipules at the leaf axil, and which could develop into flowers at a later date. The flower is grasped between the thumb and index finger and the location of the stigma determined by examining the sepals. A long, curvy sepal covers the keel, and the stigma is on the opposite side of the flower. The calyx is removed by grasping a sepal with the forceps, pulling it down and around the flower, and repeating the procedure until the five sepals are removed. The exposed corolla is removed by grasping it just above the calyx scar, then lifting and wiggling the forceps simultaneously. Care is taken to grasp the corolla low enough to remove the keel petals without injuring the stigma. The ring of anthers is visible after the corolla is removed, unless the anthers were removed with the petals. Cross-pollination can then be carried out using, for example, petri dishes or envelopes in which male flowers have been collected. Desiccators containing calcium chloride crystals are used in some environments to dry male flowers to obtain adequate pollen shed.

It has been demonstrated that emasculation is unnecessary to prevent self-pollination (Walker et al., *Crop Sci.*, 19:285-286, 1979). When emasculation is not used, the anthers near the stigma frequently are removed to make it clearly visible for pollination. The female flower usually is hand-pollinated immediately after it is prepared; although a delay of several hours does not seem to reduce seed set. Pollen shed typically begins in the morning and may end when temperatures are above 30° C., or may begin later and continue throughout much of the day with more moderate temperatures.

Pollen is available from a flower with a recently opened corolla, but the degree of corolla opening associated with pollen shed may vary during the day. In many environments, it is possible to collect male flowers and use them immediately without storage. In the southern U.S. and other humid climates, pollen shed occurs in the morning when female flowers are more immature and difficult to manipulate than in the afternoon, and the flowers may be damp from heavy dew. In those circumstances, male flowers are collected into envelopes or petri dishes in the morning and the open container is typically placed in a desiccator for about 4 h at a temperature of about 25° C. The desiccator may be taken to the field in the afternoon and kept in the shade to prevent excessive temperatures from developing within it. Pollen viability can be maintained in flowers for up to 2 days when stored at about 5° C. In a desiccator at 3° C., flowers can be stored successfully for several weeks; however, varieties may differ in the percentage of pollen that germinates after long-term storage (Kuehl, "Pollen viability and stigma receptivity of *Glycine max* (L.) Merrill," Thesis, North Carolina State College, Raleigh, N.C., 1961).

Either with or without emasculation of the female flower, hand pollination can be carried out by removing the stamens and pistil with a forceps from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

When male flowers do not have to be collected and dried in a desiccator, it may be desired to plant the parents of a cross adjacent to each other. Plants usually are grown in rows 65 to 100 cm apart to facilitate movement of personnel within the field nursery. Yield of self-pollinated seed from an individual plant may range from a few seeds to more than 1,000 as a function of plant density. A density of 30 plants/m of row can be used when 30 or fewer seeds per plant is adequate, 10 plants/m can be used to obtain about 100 seeds/plant, and 3 plants/m usually results in maximum seed production per plant. Densities of 12 plants/m or less commonly are used for artificial hybridization.

Multiple planting dates about 7 to 14 days apart usually are used to match parents of different flowering dates. When differences in flowering dates are extreme between parents, flowering of the later parent can be hastened by creating an artificially short day or flowering of the earlier parent can be delayed by use of artificially long days or delayed planting. For example, crosses with genotypes adapted to the southern U.S. are made in northern U.S. locations by covering the late genotype with a box, large can, or similar container to create an artificially short photoperiod of about 12 h for about 15 days beginning when there are three nodes with trifoliate leaves on the main stem. Plants induced to flower early tend to have flowers that self-pollinate when they are small and can be difficult to prepare for hybridization.

Grafting can be used to hasten the flowering of late flowering genotypes. A scion from a late genotype grafted on a stock that has begun to flower will begin to bloom up to 42 days earlier than normal (Kiihl et al., *Crop Sci.*, 17:181-182, 1977). First flowers on the scion appear from 21 to 50 days after the graft.

Observing pod development 7 days after pollination generally is adequate to identify a successful cross. Abortion of pods and seeds can occur several weeks after pollination, but the percentage of abortion usually is low if plant stress is minimized (Shibles et al., "Soybean," In: *Crop Physiology, Some Case Histories*, Evans (ed), Cambridge Univ. Press, Cambridge, England, 51-189, 1975). Pods that develop from artificial hybridization can be distinguished from self-pollinated pods by the presence of the calyx scar, caused by removal of the sepals. The sepals begin to fall off as the pods mature; therefore, harvest should be completed at or immediately before the time the pods reach their mature color. Harvesting pods early also avoids any loss by shattering.

Once harvested, pods are typically air-dried at not more than 38° C. until the seeds contain 13% moisture or less, then the seeds are removed by hand. Seed can be stored satisfactorily at about 25° C. for up to a year if relative humidity is 50% or less. In humid climates, germination percentage declines rapidly unless the seed is dried to 7% moisture and stored in an air-tight container at room temperature. Long-term storage in any climate is best accomplished by drying seed to 7% moisture and storing it at 10° C. or less in a room maintained at 50% relative humidity or in an air-tight container.

II. Further Embodiments of the Invention

In certain aspects of the invention, plants of soybean variety A1026138 are modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. By essentially all of the morphological and physiological characteristics, it is meant that the characteristics of a plant are recovered that are otherwise present when compared in the same environment, other than occasional variant traits that might arise during backcrossing or direct introduction of a transgene. It is understood that a locus introduced by backcrossing may or may not be transgenic in origin, and thus the term backcrossing specifically includes backcrossing to introduce loci that were created by genetic transformation.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the transferred locus from the nonrecurrent parent.

The selection of a suitable recurrent parent is an important step for a successful backcrossing procedure. The goal of a backcross protocol is to alter or substitute a trait or characteristic in the original variety. To accomplish this, a locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable, agronomically important trait to the plant. The exact backcross protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Soybean varieties can also be developed from more than two parents (Fehr, In: "*Soybeans: Improvement, Production and Uses,*" 2nd Ed., *Manograph* 16:249, 1987). The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many traits have been identified that are not regularly selected for in the development of a new inbred but that can be improved by backcrossing techniques. Traits may or may not be transgenic; examples of these traits include, but are not limited to, male sterility, herbicide resistance, resistance to bacterial, fungal, or viral disease, insect and pest resistance, restoration of male fertility, enhanced nutritional quality, yield stability, and yield enhancement. These comprise genes generally inherited through the nucleus.

Direct selection may be applied where the locus acts as a dominant trait. An example of a dominant trait is the herbicide resistance trait. For this selection process, the progeny of the initial cross are sprayed with the herbicide prior to the backcrossing. The spraying eliminates any plants which do not have the desired herbicide resistance characteristic, and only those plants which have the herbicide resistance gene are used in the subsequent backcross. This process is then repeated for all additional backcross generations.

Selection of soybean plants for breeding is not necessarily dependent on the phenotype of a plant and instead can be based on genetic investigations. For example, one may utilize a suitable genetic marker which is closely associated with a trait of interest. One of these markers may therefore be used to identify the presence or absence of a trait in the offspring of a particular cross, and hence may be used in selection of progeny for continued breeding. This technique may commonly be referred to as marker assisted selection. Any other type of genetic marker or other assay which is able to identify the relative presence or absence of a trait of interest in a plant may also be useful for breeding purposes. Procedures for marker assisted selection applicable to the breeding of soybeans are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., *Nucleic Acids Res.,* 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280:1077-1082, 1998).

Many qualitative characters also have potential use as phenotype-based genetic markers in soybeans; however, some or many may not differ among varieties commonly used as parents (Bernard and Weiss, "Qualitative genetics," In: *Soybeans: Improvement, Production, and Uses*, Caldwell (ed), *Am. Soc. of Agron.*, Madison, Wis., 117-154, 1973). The most widely used genetic markers are flower color (purple dominant to white), pubescence color (brown dominant to gray), and pod color (brown dominant to tan). The association of purple hypocotyl color with purple flowers and green hypocotyl color with white flowers is commonly used to identify hybrids in the seedling stage. Differences in maturity, height, hilum color, and pest resistance between parents can also be used to verify hybrid plants.

Many useful traits that can be introduced by backcrossing, as well as directly into a plant, are those which are introduced by genetic transformation techniques. Genetic transformation may therefore be used to insert a selected transgene into the soybean variety of the invention or may, alternatively, be used for the preparation of transgenes which can be introduced by backcrossing. Methods for the transformation of many economically important plants, including soybeans, are well known to those of skill in the art. Techniques which may be employed for the genetic transformation of soybeans include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

Protoplasts may also be employed for electroporation transformation of plants (Bates, *Mol. Biotechnol.*, 2(2):135-145, 1994; Lazzeri, *Methods Mol. Biol.*, 49:95-106, 1995). For example, the generation of transgenic soybean plants by electroporation of cotyledon-derived protoplasts was described by Dhir and Widholm in Intl. Pat. App. Publ. No. WO 92/17598, the disclosure of which is specifically incorporated herein by reference.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and often, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target soybean cells. The screen disperses the particles so that they are not delivered to the recipient cells in large aggregates. It is believed that a screen intervening between the projectile apparatus and the cells to be bombarded reduces the size of the projectile aggregate and may contribute to a higher frequency of transformation by reducing the damage inflicted on the recipient cells by projectiles that are too large.

Microprojectile bombardment techniques are widely applicable, and may be used to transform virtually any plant species. The application of microprojectile bombardment for the transformation of soybeans is described, for example, in U.S. Pat. No. 5,322,783, the disclosure of which is specifically incorporated herein by reference in its entirety.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Bio. Tech.*, 3(7):637-642, 1985). Moreover, recent technological advances in vectors for *Agrobacterium*-mediated gene transfer have improved the arrangement of genes and cloning sites in the vectors to facilitate the construction of vectors capable of expressing various polypeptide coding genes. Vectors can have convenient multiple-cloning sites (MCS) flanked by a promoter and a polyadenylation site for direct expression of inserted polypeptide coding genes. Other vectors can comprise site-specific recombination sequences, enabling insertion of a desired DNA sequence without the use of restriction enzymes (Curtis et al., *Plant Physiology* 133:462-469, 2003). Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio. Tech.*, 3(7):629-635, 1985; U.S. Pat. No. 5,563,055). Use of *Agrobacterium* in the context of soybean transformation has been described, for example, by Chee and Slightom (*Methods Mol. Biol.*, 44:101-119, 1995) and in U.S. Pat. No. 5,569,834, the disclosures of which are specifically incorporated herein by reference in their entirety.

Transformation of plant protoplasts also can be achieved using methods based on calcium phosphate precipitation, polyethylene glycol treatment, electroporation, and combinations of these treatments (see, e.g., Potrykus et al., *Mol. Gen. Genet.*, 199(2):169-177, 1985; Omirulleh et al., *Plant Mol. Biol.*, 21(3):415-428, 1993; Fromm et al., *Nature*, 319(6056): 791-793, 1986; Uchimiya et al., *Mol. Gen. Genet.*, 204(2): 204-207, 1986; Marcotte et al., *Nature*, 335(6189):454-457, 1988). The demonstrated ability to regenerate soybean plants from protoplasts makes each of these techniques applicable to soybean (Dhir et al., *Plant Cell Rep.*, 10(2):97-101, 1991).

Many hundreds if not thousands of different genes are known and could potentially be introduced into a soybean plant according to the invention. Non-limiting examples of particular genes and corresponding phenotypes one may choose to introduce into a soybean plant are presented below.

A. Herbicide Resistance

Numerous herbicide resistance genes are known and may be employed with the invention. An example is a gene conferring resistance to a herbicide that inhibits the growing point or meristem, such as an imidazalinone or a sulfonylurea. Exemplary genes in this category code for mutant ALS and AHAS enzyme as described, for example, by Lee et al., *EMBO J.*, 7:1241, 1988; Gleen et al., *Plant Molec. Biology*, 18:1185-1187, 1992; and Miki et al., *Theor. Appl. Genet.*, 80:449, 1990.

Resistance genes for glyphosate (resistance conferred by mutant 5-enolpyruvl-3 phosphikimate synthase (EPSPS) and aroA genes, respectively) and other phosphono compounds such as glufosinate (phosphinothricin acetyl transferase (PAT) and *Streptomyces hygroscopicus* phosphinothricin-acetyl transferase (bar) genes) may also be used. See, for example, U.S. Pat. No. 4,940,835 to Shah et al., which discloses the nucleotide sequence of a form of EPSPS which can confer glyphosate resistance. Examples of specific EPSPS transformation events conferring glyphosate resistance are provided by U.S. Pat. Nos. 6,040,497 and 7,632,985. The MON89788 event disclosed in U.S. Pat. No. 7,632,985 in particular is beneficial in conferring glyphosate tolerance in combination with an increase in average yield relative to prior events.

A DNA molecule encoding a mutant aroA gene can be obtained under ATCC Accession Number 39256, and the nucleotide sequence of the mutant gene is disclosed in U.S. Pat. No. 4,769,061 to Comai. A hygromycin B phosphotransferase gene from *E. coli* which confers resistance to glyphosate in tobacco callus and plants is described in Penaloza-Vazquez et al., *Plant Cell Reports*, 14:482-487, 1995. European Patent Application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyltransferase gene is provided in European Patent Application No. 0 242 246 to Leemans et al. DeGreef et al. (*Biotechnology*, 7:61, 1989), describe the production of transgenic plants that express chimeric bar genes coding for phosphinothricin acetyl transferase activity. Exemplary genes conferring resistance to phenoxy propionic acids and cyclohexones, such as sethoxydim and haloxyfop are the Acct-S1, Acct-S2 and Acct-S3 genes described by Marshall et al., (*Theor. Appl. Genet.*, 83:4:35, 1992).

Genes are also known conferring resistance to a herbicide that inhibits photosynthesis, such as a triazine (psbA and gs+ genes) and a benzonitrile (nitrilase gene). Przbila et al. (*Plant Cell*, 3:169, 1991) describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al. (*Biochem. J.*, 285(Pt 1):173-180, 1992). Protoporphyrinogen oxidase (PPO) is the target of the PPO-inhibitor class of herbicides; a PPO-inhibitor resistant PPO gene was recently identified in *Amaranthus tuberculatus* (Patzoldt et al., *PNAS*, 103(33):12329-2334, 2006). The herbicide methyl viologen inhibits $CO_2$ assimilation. Foyer et al. (*Plant Physiol.*, 109: 1047-1057, 1995) describe a plant overexpressing glutathione reductase (GR) which is resistant to methyl viologen treatment.

Siminszky (*Phytochemistry Reviews*, 5:445-458, 2006) describes plant cytochrome P450-mediated detoxification of multiple, chemically unrelated classes of herbicides.

Bayley et al. (*Theor. Appl. Genet.*, 83:645-649, 1992) describe the creation of 2,4-D-resistant transgenic tobacco and cotton plants using the 2,4-D monooxygenase gene tfdA from *Alcaligenes eutrophus* plasmid pJP5. U.S. Pat. App. Pub. No. 20030135879 describes the isolation of a gene for dicamba monooxygenase (DMO) from *Psueodmonas maltophilia* that is involved in the conversion of dicamba to a non-toxic 3,6-dichlorosalicylic acid and thus may be used for producing plants tolerant to this herbicide.

Other examples of herbicide resistance have been described, for instance, in U.S. Pat. Nos. 6,803,501; 6,448, 476; 6,248,876; 6,225,114; 6,107,549; 5,866,775; 5,804,425; 5,633,435; 5,463,175.

B. Disease and Pest Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al. (*Science*, 266:7891, 1994) (cloning of the tomato Cf-9 gene for resistance to *Cladosporium fulvum*); Martin et al. (*Science*, 262: 1432, 1993) (tomato Pto gene for resistance to *Pseudomonas syringae* pv. tomato); and Mindrinos et al. (*Cell*, 78(6):1089-1099, 1994) (*Arabidopsis* RPS2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (*Ann. Rev. Phytopathol.*, 28:451, 1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody may also be used. See, for example, Tavladoraki et al. (*Nature*, 366:469, 1993), who show that transgenic plants expressing recombinant antibody genes are protected from virus attack. Virus resistance has also been described in, for example, U.S. Pat. Nos. 6,617,496; 6,608,241; 6,015,940; 6,013,864; 5,850,023 and 5,304,730. Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or by increasing salicylic acid production (Ryals et al., *Plant Cell*, 8:1809-1819, 1996).

Logemann et al. (*Biotechnology*, 10:305, 1992), for example, disclose transgenic plants expressing a barley ribosome-inactivating gene that have an increased resistance to fungal disease. Plant defensins may be used to provide resistance to fungal pathogens (Thomma et al., *Planta*, 216:193-202, 2002). Other examples of fungal disease resistance are provided in U.S. Pat. Nos. 6,653,280; 6,573,361; 6,506,962; 6,316,407; 6,215,048; 5,516,671; 5,773,696; 6,121,436; and 6,316,407.

Nematode resistance has been described, for example, in U.S. Pat. No. 6,228,992, and bacterial disease resistance has been described in U.S. Pat. No. 5,516,671.

The use of the herbicide glyphosate for disease control in soybean plants containing event MON89788, which confers glyphosate tolerance, has also been described in U.S. Pat. No. 7,608,761.

C. Insect Resistance

One example of an insect resistance gene includes a *Bacillus thuringiensis* protein, a derivative thereof or a synthetic polypeptide modeled thereon. See, for example, Geiser et al. (*Gene*, 48(1):109-118, 1986), who disclose the cloning and nucleotide sequence of a *Bacillus thuringiensis* δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al. (*Plant Molec. Biol.*, 24:25, 1994), who disclose the nucleotide sequences of several *Clivia miniata* mannose-binding lectin genes. A vitamin-binding protein may also be used, such as avidin. See PCT Application No. US93/06487, the contents of which are hereby incorporated by reference. This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al. (*J. Biol. Chem.*, 262: 16793, 1987) (nucleotide sequence of rice cysteine proteinase inhibitor), Huub et al. (*Plant Molec. Biol.*, 21:985, 1993) (nucleotide sequence of cDNA encoding tobacco proteinase inhibitor I), and Sumitani et al. (*Biosci. Biotech. Biochem.*, 57:1243, 1993) (nucleotide sequence of *Streptomyces nitrosporeus* α-amylase inhibitor).

An insect-specific hormone or pheromone may also be used. See, for example, the disclosure by Hammock et al. (*Nature*, 344:458, 1990), of baculovirus expression of cloned juvenile hormone esterase, an inactivator of juvenile hormone; Gade and Goldsworthy (*Eds. Physiological System in Insects*, Elsevier Academic Press, Burlington, Mass., 2007), describing allostatins and their potential use in pest control; and Palli et al. (*Vitam. Horm.*, 73:59-100, 2005), disclosing use of ecdysteroid and ecdysteroid receptor in agriculture. The diuretic hormone receptor (DHR) was identified in Price et al. (*Insect Mol. Biol.*, 13:469-480, 2004) as a candidate target of insecticides.

Still other examples include an insect-specific antibody or an immunotoxin derived therefrom and a developmental-arrestive protein. See Taylor et al. (Seventh Int'l Symposium on Molecular Plant-Microbe Interactions, Edinburgh, Scotland, Abstract W97, 1994), who described enzymatic inactivation in transgenic tobacco via production of single-chain antibody fragments. Numerous other examples of insect resistance have been described. See, for example, U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245 and 5,763,241.

D. Male Sterility

Genetic male sterility is available in soybeans and can increase the efficiency with which hybrids are made, in that it can eliminate the need to physically emasculate the soybean plant used as a female in a given cross. (Brim and Stuber, *Crop Sci.*, 13:528-530, 1973). Herbicide-inducible male sterility systems have also been described. (U.S. Pat. No. 6,762,344).

Where one desires to employ male-sterility systems, it may be beneficial to also utilize one or more male-fertility restorer genes. For example, where cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the soybean plant is utilized, but in many cases the seeds will be deemed the most valuable portion of the crop, so fertility of the hybrids in these crops must be restored. Therefore, one aspect of the current invention concerns plants of the soybean variety A1026138 comprising a genetic locus capable of restoring male fertility in an otherwise male-sterile plant. Examples of male-sterility genes and corresponding restorers which could be employed with the plants of the invention are well known to those of skill in the art of plant breeding (see, e.g., U.S. Pat. Nos. 5,530,191 and 5,684,242, the disclosures of which are each specifically incorporated herein by reference in their entirety).

E. Modified Fatty Acid, Phytate and Carbohydrate Metabolism

Genes may be used conferring modified fatty acid metabolism. For example, stearyl-ACP desaturase genes may be used. See Knutzon et al. (*Proc. Natl. Acad. Sci. USA*, 89:2624, 1992). Various fatty acid desaturases have also been described. McDonough et al. describe a *Saccharomyces cerevisiae* OLE1 gene encoding Δ9-fatty acid desaturase, an enzyme which forms the monounsaturated palmitoleic (16:1) and oleic (18:1) fatty acids from palmitoyl (16:0) or stearoyl (18:0) CoA (*J. Biol. Chem.*, 267(9):5931-5936, 1992). Fox et al. describe a gene encoding a stearoyl-acyl carrier protein delta-9 desaturase from castor (*Proc. Natl. Acad. Sci. USA*, 90(6):2486-2490, 1993). Reddy et al. describe Δ6- and Δ12-desaturases from the cyanobacteria *Synechocystis* responsible for the conversion of linoleic acid (18:2) to gamma-linolenic acid (18:3 gamma) (*Plant Mol. Biol.*, 22(2):293-300, 1993). A gene from *Arabidopsis thaliana* that encodes an omega-3 desaturase has been identified (Arondel et al. *Science*, 258(5086):1353-1355, 1992). Plant A9-desaturases (PCT Application Publ. No. WO 91/13972) and soybean and *Brassica* A15-desaturases (European Patent Application Publ. No. EP 0616644) have also been described. U.S. Pat. No. 7,622,632 describes fungal Δ15-desaturases and their use in plants. EP Patent No. 1656449 describes Δ6-desaturases from *Primula* as well as soybean plants having an increased stearidonic acid (SDA, 18:4) content. U.S. Pat. App. Pub. No. 2008-0260929 describes expression of transgenic desaturase enzymes in corn plants, and improved fatty acid profiles resulting therefrom.

Modified oil production is disclosed, for example, in U.S. Pat. Nos. 6,444,876; 6,426,447 and 6,380,462. High oil production is disclosed, for example, in U.S. Pat. Nos. 6,495,739; 5,608,149; 6,483,008 and 6,476,295. Modified fatty acid content is disclosed, for example, in U.S. Pat. Nos. 6,828,475; 6,822,141; 6,770,465; 6,706,950; 6,660,849; 6,596,538; 6,589,767; 6,537,750; 6,489,461 and 6,459,018.

Phytate metabolism may also be modified by introduction of a phytase-encoding gene to enhance breakdown of phytate, adding more free phosphate to the transformed plant. For example, see Van Hartingsveldt et al. (*Gene*, 127:87, 1993), for a disclosure of the nucleotide sequence of an *Aspergillus niger* phytase gene. In soybean, this, for example, could be accomplished by cloning and then reintroducing DNA associated with the single allele which is responsible for soybean mutants characterized by low levels of phytic acid. See Raboy et al. (*Plant Physiol.*, 124(1):355-368, 2000).

A number of genes are known that may be used to alter carbohydrate metabolism. For example, plants may be transformed with a gene coding for an enzyme that alters the branching pattern of starch. See Shiroza et al. (*J. Bacteriol.*, 170:810, 1988) (nucleotide sequence of *Streptococcus mutans* fructosyltransferase gene), Steinmetz et al. (*Mol. Gen. Genet.*, 20:220, 1985) (nucleotide sequence of *Bacillus subtilis* levansucrase gene), Pen et al. (*Biotechnology*, 10:292, 1992) (production of transgenic plants that express *Bacillus licheniformis* α-amylase), Elliot et al. (*Plant Molec. Biol.*, 21:515, 1993) (nucleotide sequences of tomato invertase genes), Sergaard et al. (*J. Biol. Chem.*, 268:22480, 1993) (site-directed mutagenesis of barley α-amylase gene), and Fisher et al. (*Plant Physiol.*, 102:1045, 1993) (maize endosperm starch branching enzyme II). The Z10 gene encoding a 10 kD zein storage protein from maize may also be used to alter the quantities of 10 kD zein in the cells relative to other components (Kirihara et al., *Gene*, 71(2):359-370, 1988).

F. Resistance to Abiotic Stress

Abiotic stress includes dehydration or other osmotic stress, salinity, high or low light intensity, high or low temperatures, submergence, exposure to heavy metals, and oxidative stress. Delta-pyrroline-5-carboxylate synthetase (P5CS) from mothbean has been used to provide protection against general osmotic stress. Mannitol-1-phosphate dehydrogenase (mt1D) from *E. coli* has been used to provide protection against drought and salinity. Choline oxidase (codA from *Arthrobactor globiformis*) can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levan sucrase (SacB) from yeast and *Bacillus subtilis*, respectively, can provide protection against drought (summarized from Annex II Genetic Engineering for Abiotic Stress Tolerance in Plants, Consultative Group On International Agricultural Research Technical Advisory Committee). Overexpression of superoxide dismutase can be used to protect against superoxides, as described in U.S. Pat. No. 5,538,878 to Thomas et al.

G. Additional Traits

Additional traits can be introduced into the soybean variety of the present invention. A non-limiting example of such a trait is a coding sequence which decreases RNA and/or protein levels. The decreased RNA and/or protein levels may be achieved through RNAi methods, such as those described in U.S. Pat. No. 6,506,559 to Fire and Mellow.

Another trait that may find use with the soybean variety of the invention is a sequence which allows for site-specific recombination. Examples of such sequences include the FRT sequence, used with the FLP recombinase (Zhu and Sadowski, *J. Biol. Chem.*, 270:23044-23054, 1995); and the LOX sequence, used with CRE recombinase (Sauer, *Mol. Cell. Biol.*, 7:2087-2096, 1987). The recombinase genes can be encoded at any location within the genome of the soybean plant, and are active in the hemizygous state.

It may also be desirable to make soybean plants more tolerant to or more easily transformed with *Agrobacterium tumefaciens*. Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases (reviewed in Gelvin, *Microbiology & Mol. Biol. Reviews*, 67:16-37, 2003).

In addition to the modification of oil, fatty acid or phytate content described above, it may additionally be beneficial to modify the amounts or levels of other compounds. For example, the amount or composition of antioxidants can be altered. See, for example, U.S. Pat. No. 6,787,618; U.S. Pat. App. Pub. No. 20040034886 and International Patent App. Pub. No. WO 00/68393, which disclose the manipulation of antioxidant levels, and International Patent App. Pub. No. WO 03/082899, which discloses the manipulation of a antioxidant biosynthetic pathway.

Additionally, seed amino acid content may be manipulated. U.S. Pat. No. 5,850,016 and International Patent App. Pub. No. WO 99/40209 disclose the alteration of the amino acid compositions of seeds. U.S. Pat. Nos. 6,080,913 and 6,127,600 disclose methods of increasing accumulation of essential amino acids in seeds.

U.S. Pat. No. 5,559,223 describes synthetic storage proteins in which the levels of essential amino acids can be manipulated. International Patent App. Pub. No. WO 99/29882 discloses methods for altering amino acid content of proteins. International Patent App. Pub. No. WO 98/20133 describes proteins with enhanced levels of essential amino acids. International Patent App. Pub. No. WO 98/56935 and U.S. Pat. Nos. 6,346,403, 6,441,274 and 6,664,445 disclose plant amino acid biosynthetic enzymes. International Patent App. Pub. No. WO 98/45458 describes synthetic seed proteins having a higher percentage of essential amino acids than wild-type.

U.S. Pat. No. 5,633,436 discloses plants comprising a higher content of sulfur-containing amino acids; U.S. Pat. No. 5,885,801 discloses plants comprising a high threonine content; U.S. Pat. Nos. 5,885,802 and 5,912,414 disclose plants comprising a high methionine content; U.S. Pat. No. 5,990,389 discloses plants comprising a high lysine content; U.S. Pat. No. 6,459,019 discloses plants comprising an increased lysine and threonine content; International Patent App. Pub. No. WO 98/42831 discloses plants comprising a high lysine content; International Patent App. Pub. No. WO 96/01905 discloses plants comprising a high threonine content and International Patent App. Pub. No. WO 95/15392 discloses plants comprising a high lysine content.

III. Origin and Breeding History of an Exemplary Single Locus Converted Plant It is known to those of skill in the art that, by way of the technique of backcrossing, one or more traits may be introduced into a given variety while otherwise retaining essentially all of the traits of that variety. An example of such backcrossing to introduce a trait into a starting variety is described in U.S. Pat. No. 6,140,556, the entire disclosure of which is specifically incorporated herein by reference. The procedure described in U.S. Pat. No. 6,140,556 can be summarized as follows: The soybean variety known as Williams '82 [*Glycine max* L. Merr.] (Reg. No. 222, PI 518671) was developed using backcrossing techniques to transfer a locus comprising the $Rps_1$ gene to the variety Williams (Bernard and Cremeens, *Crop Sci.*, 28:1027-1028, 1988). Williams '82 is a composite of four resistant lines from the $BC_6F_3$ generation, which were selected from 12 field-tested resistant lines from Williams×Kingwa. The variety Williams was used as the recurrent parent in the backcross and the variety Kingwa was used as the source of the $Rps_1$ locus. This gene locus confers resistance to 19 of the 24 races of the fungal agent phytopthora rot.

The $F_1$ or $F_2$ seedlings from each backcross round were tested for resistance to the fungus by hypocotyl inoculation using the inoculum of race 5. The final generation was tested using inoculum of races 1 to 9. In a backcross such as this, where the desired characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield. As in this example, lines with the phenotype of the recurrent parent may be composited without the usual replicated tests for traits such as yield, protein or oil percentage in the individual lines.

The variety Williams '82 is comparable to the recurrent parent variety Williams in its traits except resistance to phytopthora rot. For example, both varieties have a relative maturity of 38, indeterminate stems, white flowers, brown pubescence, tan pods at maturity and shiny yellow seeds with black to light black hila.

IV. Tissues Cultures and in Vitro Regeneration of Soybean Plants

A further aspect of the invention relates to tissue cultures of the soybean variety designated A1026138. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, leaves, roots, root tips, anthers, and the like. In one embodiment, the tissue culture comprises embryos, protoplasts, meristematic cells, pollen, leaves or anthers.

Exemplary procedures for preparing tissue cultures of regenerable soybean cells and regenerating soybean plants therefrom, are disclosed in U.S. Pat. Nos. 4,992,375; 5,015,580; 5,024,944 and 5,416,011, each of the disclosures of which is specifically incorporated herein by reference in its entirety.

An important ability of a tissue culture is the capability to regenerate fertile plants. This allows, for example, transformation of the tissue culture cells followed by regeneration of transgenic plants. For transformation to be efficient and successful, DNA must be introduced into cells that give rise to plants or germ-line tissue.

Soybeans typically are regenerated via two distinct processes: shoot morphogenesis and somatic embryogenesis (Finer, Cheng, Verma, "Soybean transformation: Technologies and progress," In: *Soybean: Genetics, Molecular Biology and Biotechnology*, CAB Intl, Verma and Shoemaker (ed), Wallingford, Oxon, UK, 250-251, 1996). Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos. Lines that produce large numbers of embryos during an 'induction' step may not give rise to rapidly-growing proliferative cultures. Therefore, it may be desired to optimize tissue culture conditions for each soybean line.

These optimizations may readily be carried out by one of skill in the art of tissue culture through small-scale culture studies. In addition to line-specific responses, proliferative cultures can be observed with both shoot morphogenesis and somatic embryogenesis. Proliferation is beneficial for both systems, as it allows a single, transformed cell to multiply to the point that it will contribute to germ-line tissue.

Shoot morphogenesis was first reported by Wright et al. (*Plant Cell Reports,* 5:150-154, 1986) as a system whereby shoots were obtained de novo from cotyledonary nodes of soybean seedlings. The shoot meristems were formed subepidermally and morphogenic tissue could proliferate on a medium containing benzyl adenine (BA). This system can be used for transformation if the subepidermal, multicellular origin of the shoots is recognized and proliferative cultures are utilized. The idea is to target tissue that will give rise to new shoots and proliferate those cells within the meristematic tissue to lessen problems associated with chimerism. Formation of chimeras, resulting from transformation of only a single cell in a meristem, are problematic if the transformed cell is not adequately proliferated and does not does not give rise to germ-line tissue. Once the system is well understood and reproduced satisfactorily, it can be used as one target tissue for soybean transformation.

Somatic embryogenesis in soybean was first reported by Christianson et al. (*Science,* 222:632-634, 1983) as a system in which embryogenic tissue was initially obtained from the zygotic embryo axis. These embryogenic cultures were proliferative but the repeatability of the system was low and the origin of the embryos was not reported. Later histological studies of a different proliferative embryogenic soybean culture showed that proliferative embryos were of apical or surface origin with a small number of cells contributing to embryo formation. The origin of primary embryos (the first embryos derived from the initial explant) is dependent on the explant tissue and the auxin levels in the induction medium (Hartweck et al., *In Vitro Cell. Develop. Bio.,* 24:821-828, 1988). With proliferative embryonic cultures, single cells or small groups of surface cells of the 'older' somatic embryos form the 'newer' embryos.

Embryogenic cultures can also be used successfully for regeneration, including regeneration of transgenic plants, if the origin of the embryos is recognized and the biological limitations of proliferative embryogenic cultures are understood. Biological limitations include the difficulty in developing proliferative embryogenic cultures and reduced fertility problems (culture-induced variation) associated with plants regenerated from long-term proliferative embryogenic cultures. Some of these problems are accentuated in prolonged cultures. The use of more recently cultured cells may decrease or eliminate such problems.

V. Definitions

In the description and tables, a number of terms are used. In order to provide a clear and consistent understanding of the specification and claims, the following definitions are provided:

A: When used in conjunction with the word "comprising" or other open language in the claims, the words "a" and "an" denote "one or more."

Allele: Any of one or more alternative forms of a gene locus, all of which relate to one trait or characteristic. In a diploid cell or organism, the two alleles of a given gene occupy corresponding loci on a pair of homologous chromosomes.

Aphids: Aphid resistance is scored on a scale from 1 to 9; a score of 4 or less indicates resistance. Varieties scored as 1 to 5 appear normal and healthy, with numbers of aphids increasing from none to up to 300 per plant. A score of 7 indicates that there are 301 to 800 aphids per plant and that the plants show slight signs of infestation. A score of 9 indicates severe infestation and stunted plants with severely curled and yellow leaves.

Asian Soybean Rust (ASR): ASR may be visually scored from 1 to 5, where 1=immune; 2=leaf exhibits red/brown lesions over less than 50% of surface; 3=leaf exhibits red/brown lesions over greater than 50% of surface; 4=leaf exhibits tan lesions over less than 50% of surface; and 5=leaf exhibits tan lesions over greater than 50% of surface. Resistance to ASR may be characterized phenotypically as well as genetically. Soybean plants phenotypically characterized as resistant to ASR typically exhibit red brown lesions covering less than 25% of the leaf. Genetic characterization of ASR resistance may be carried out, for example, by identifying the presence in a soybean plant of one or more genetic markers linked to the ASR resistance.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Brown Stem Rot (BSR): Brown stem rot is visually scored from 1 to 9 comparing all genotypes in a given test, with a score of 1 indicating no symptoms, and 9 indicating severe symptoms of leaf yellowing and necrosis. The score is based on leaf symptoms of yellowing and necrosis caused by brown stem rot. Plants may be identified as "resistant" or "moderately resistant" to BSR.

Chloride Sensitivity: Plants may be categorized as "includers" or "excluders" with respect to chloride sensitivity. Excluders display increased tolerance to elevated soil chloride levels compared to includers. In addition, excluders tend to partition chloride in the root systems and reduce the amount of chloride transported to more sensitive, aboveground tissues.

Chromatography: A technique wherein a mixture of dissolved substances are bound to a solid support followed by passing a column of fluid across the solid support and varying the composition of the fluid. The components of the mixture are separated by selective elution.

Crossing: The mating of two parent plants.

Cross-pollination: Fertilization by the union of two gametes from different plants.

Emasculate: The removal of plant male sex organs or the inactivation of the organs with a cytoplasmic or nuclear genetic factor or a chemical agent conferring male sterility.

Emergence (EMR): The emergence score describes the ability of a seed to emerge from the soil after planting. Each genotype is given a 1 to 9 score based on its percent of emergence. A score of 1 indicates an excellent rate and percent of emergence, an intermediate score of 5 indicates an average rating and a 9 score indicates a very poor rate and percent of emergence.

Enzymes: Molecules which can act as catalysts in biological reactions.

$F_1$ Hybrid: The first generation progeny of the cross of two nonisogenic plants.

Frog Eye Leaf Spot (also known as *Cercospora* Leaf Spot): is caused by *Cercospora sojina*. Symptoms occur mostly on foliage. Upper surface of leaf: Dark, water soaked spots with or without a lighter center and develop into brown spots surrounded by a narrow dark reddish brown margin. Lesions become ash gray to light brown. Lower surface of leaf: spots are darker with light to dark gray centers and sporulate. Non sporulating lesions are light to dark brown and translucent with a paper white center. Each sample is evaluated by assigning one score for incidence and one for severity. The final rating is determined by a mathematical equation using the incidence score and severity score resulting in a ranking/rating of 1 (or High Susceptibility) to 5 (or Resistant).

Genotype: The genetic constitution of a cell or organism.

Haploid: A cell or organism having one set of the two sets of chromosomes in a diploid.

Iron-Deficiency Chlorosis (IDE=early; IDL=late): Iron-deficiency chlorosis is scored in a system ranging from 1 to 9 based on visual observations. A score of 1 means no stunting of the plants or yellowing of the leaves and a score of 9 indicates the plants are dead or dying caused by iron-deficiency chlorosis; a score of 5 means plants have intermediate health with some leaf yellowing.

Linkage: A phenomenon wherein alleles on the same chromosome tend to segregate together more often than expected by chance if their transmission was independent.

Linolenic Acid Content (LLN): Low-linolenic acid soybean oil contains three percent or less linolenic acid, compared to eight percent linolenic acid for traditional soybeans.

Lodging Resistance (LDG): Lodging is rated on a scale of 1 to 9. A score of 1 indicates erect plants. A score of 5 indicates plants are leaning at a 45 degree(s) angle in relation to the ground and a score of 9 indicates plants are lying on the ground.

Marker: A readily detectable phenotype, preferably inherited in codominant fashion (both alleles at a locus in a diploid heterozygote are readily detectable), with no environmental variance component, i.e., heritability of 1.

Maturity Date (MAT): Plants are considered mature when 95% of the pods have reached their mature color. The maturity date is typically described in measured days after August 31 in the northern hemisphere.

Moisture (MST): The average percentage moisture in the seeds of the variety.

Oil or Oil Percent: Seed oil content is measured and reported on a percentage basis.

Phenotype: The detectable characteristics of a cell or organism, which characteristics are the manifestation of gene expression.

Phenotypic Score (PSC): The phenotypic score is a visual rating of the general appearance of the variety. All visual traits are considered in the score, including healthiness, standability, appearance and freedom from disease. Ratings are scored as 1 being poor to 9 being excellent.

*Phytophthora* Root Rot (PRR): Disorder in which the most recognizable symptom is stem rot. Brown discoloration ranges below the soil line and up to several inches above the soil line. Leaves often turn yellow, dull green and/or gray and may become brown and wilted, but remain attached to the plant.

*Phytophthora* Allele: Susceptibility or resistance to *Phytophthora* root rot races is affected by alleles such as Rps 1a (denotes resistance to Races 1, 2, 10, 11, 13-18, 24, 26, 27, 31, 32, and 36); Rps 1c (denotes resistance to Races 1-3, 6-11, 13, 15, 17, 21, 23, 24, 26, 28-30, 32, 34 and 36); Rps 1k (denotes resistance to Races 1-11, 13-15, 17, 18, 21-24, 26, 36 and 37); Rps2 (denotes resistance to Races 1-5, 9-29, 33, 34 and 36-39); Rps3a (denotes resistance to Races 1-5, 8, 9, 11, 13, 14, 16, 18, 23, 25, 28, 29, 31-35); Rps6 (denotes resistance to Races 1-4, 10, 12, 14-16, 18-21 and 25); and Rps7 (denotes resistance to Races 2, 12, 16, 18, 19, 33, 35 and 36).

*Phytophthora* Tolerance: Tolerance to *Phytophthora* root rot is rated on a scale of 1 to 9, with a score of 1 being the best or highest tolerance ranging down to a score of 9, which indicates the plants have no tolerance to *Phytophthora*.

Plant Height (PHT): Plant height is taken from the top of soil to the top node of the plant and is measured in inches.

Predicted Relative Maturity (PRM): The maturity grouping designated by the soybean industry over a given growing area. This figure is generally divided into tenths of a relative maturity group. Within narrow comparisons, the difference of a tenth of a relative maturity group equates very roughly to a day difference in maturity at harvest.

Protein (PRO), or Protein Percent: Seed protein content is measured and reported on a percentage basis.

Regeneration: The development of a plant from tissue culture.

Relative Maturity: The maturity grouping designated by the soybean industry over a given growing area. This figure is generally divided into tenths of a relative maturity group. Within narrow comparisons, the difference of a tenth of a relative maturity group equates very roughly to a day difference in maturity at harvest.

Seed Protein Peroxidase Activity: Seed protein peroxidase activity is defined as a chemical taxonomic technique to separate varieties based on the presence or absence of the peroxidase enzyme in the seed coat. There are two types of soybean varieties, those having high peroxidase activity (dark red color) and those having low peroxidase activity (no color).

Seed Weight (SWT): Soybean seeds vary in size; therefore, the number of seeds required to make up one pound also varies. This affects the pounds of seed required to plant a given area, and can also impact end uses. (SW100=weight in grams of 100 seeds.)

Seed Yield (Bushels/Acre): The yield in bushels/acre is the actual yield of the grain at harvest.

Seedling Vigor Rating (SDV): General health of the seedling, measured on a scale of 1 to 9, where 1 is best and 9 is worst.

Seeds per Pound: Soybean seeds vary in size; therefore, the number of seeds required to make up one pound also varies. This affects the pounds of seed required to plant a given area, and can also impact end uses.

Selection Index (SELIN): The percentage of the test mean.

Self-pollination: The transfer of pollen from the anther to the stigma of the same plant.

Shattering: The amount of pod dehiscence prior to harvest. Pod dehiscence involves seeds falling from the pods to the soil. This is a visual score from 1 to 9 comparing all genotypes within a given test. A score of 1 means pods have not opened and no seeds have fallen out. A score of 5 indicates approximately 50% of the pods have opened, with seeds falling to the ground and a score of 9 indicates 100% of the pods are opened.

Single Locus Converted (Conversion) Plant: Plants which are developed by a plant breeding technique called backcrossing, wherein essentially all of the morphological and physiological characteristics of a soybean variety are recovered in addition to the characteristics of the single locus transferred into the variety via the backcrossing technique and/or by genetic transformation.

Southern Root Knot Resistance: Resistance to Southern root knot nematode is scored as susceptible (S), moderately susceptible (MS), moderately resistant (MR) or resistant (R).

Southern Stem Canker (STC): Disorder that results in small, reddish-brown lesions near leaf node. Lesions expand to form dark brown to black sunken cankers. Leaves develop interveinal chlorosis and necrosis. Shepherd's crook formation may occur. Scoring is based on percentage of dead plants (DP). Highly susceptible (HS) score corresponds to greater than 90% DP; resistant (R) score corresponds to 0-25% DP.

Stearate: A fatty acid in soybean seeds measured and reported as a percent of the total oil content.

Substantially Equivalent: A characteristic that, when compared, does not show a statistically significant difference (e.g., p=0.05) from the mean.

Sudden Death Syndrome: Leaf symptoms appear first as bright yellow chlorotic spots, with progressive development of brown necrotic areas and eventual leaflet death. Samples are individually evaluated by assigning one score for incidence and one for severity. Plants scored as Resistant (R); Moderately Resistant (MR); Moderately Susceptible (MS); and Susceptible (S).

Tissue Culture: A composition comprising isolated cells of the same or a different type or a collection of such cells organized into parts of a plant.

Transgene: A genetic locus comprising a sequence which has been introduced into the genome of a soybean plant by transformation.

White Mold: Also known as *Sclerotinia* stem rot. Varieties scored based on relative tolerance to the disease on a 1-9 basis, where less than 4=very good; 4=good; 5=above average; 6=average; 7=below average; and greater than 7=poor.

Yield Best Estimate (YLD_BE): The adjusted yield of a plot in bushels/acre. Plot yields are adjusted using the nearest neighbor spatial covariate method first described by Papadakis (Méthode statistique pour des experiences sur champ, Thessaloniki Plant Breeding Institute Bulletin No. 23, Thessaloniki, London, 1937).

Yield Count (YLD COUNT): The number of evaluated plots.

VI. Deposit Information

A deposit of the soybean variety A1026138, which is disclosed herein above and referenced in the claims, was made with the American Type Culture Collection (ATCC), 10801 University Blvd., Manassas, Va. 20110-2209. The date of deposit is Jan. 22, 2014 and the accession number for those deposited seeds of soybean variety A1026138 is ATCC Accession No. PTA-120935. All restrictions upon the deposit have been removed, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The references cited herein, to the extent that they provide exemplary procedural or other details supplementary to those set forth herein, are specifically incorporated herein by reference.

What is claimed is:

1. A plant of soybean variety A1026138, wherein a sample of seed of said variety has been deposited under ATCC Accession No. PTA-120935.

2. A plant part of the plant of claim 1, wherein the plant part comprises at least a first cell of said plant.

3. The plant part of claim 2, further defined as pollen, a meristem, a cell, or an ovule.

4. A seed of soybean variety A1026138, wherein a sample of seed of said variety has been deposited under ATCC Accession No. PTA-120935.

5. A soybean plant that expresses all of the physiological and morphological characteristics of soybean variety A1026138, wherein a sample of seed of said variety has been deposited under ATCC Accession No. PTA-120935.

6. A method of producing soybean seed, wherein the method comprises crossing the plant of claim 1 with itself or a second soybean plant.

7. The method of claim 6, wherein the method comprises crossing the plant of soybean variety A1026138 with a second, distinct soybean plant to produce an $F_1$ hybrid soybean seed.

8. An $F_1$ hybrid soybean seed produced by the method of claim 7.

9. An $F_1$ hybrid soybean plant produced by growing the seed of claim 8.

10. A composition comprising a seed of soybean variety A1026138 comprised in plant seed growth media, wherein a sample of seed of said variety has been deposited under ATCC Accession No. PTA-120935.

11. The composition of claim 10, wherein the growth media is soil or a synthetic cultivation medium.

12. A plant produced by introducing a single locus conversion into soybean variety A1026138, or a selfed progeny thereof comprising the single locus conversion, wherein the single locus conversion was introduced into soybean variety A1026138 by backcrossing or genetic transformation and wherein a sample of seed of soybean variety A1026138 has been deposited under ATCC Accession No. PTA-120935, wherein the plant otherwise comprises essentially all of the physiological and morphological characteristics of the soybean variety A1026138.

13. The plant of claim 12, wherein the single locus conversion comprises a transgene.

14. A seed that produces the plant of claim 12.

15. The seed of claim 14, wherein the single locus confers a trait selected from the group consisting of male sterility, herbicide tolerance, insect resistance, pest resistance, disease resistance, modified fatty acid metabolism, abiotic stress resistance, altered seed amino acid composition, site-specific genetic recombination, and modified carbohydrate metabolism.

16. The seed of claim 15, wherein the single locus confers tolerance to an herbicide selected from the group consisting of glyphosate, sulfonylurea, imidazalinone, dicamba, glufosinate, phenoxy proprionic acid, cyclohexanedione, triazine, benzonitrile, PPO-inhibitor herbicides and broxynil.

17. The seed of claim 15, wherein the single locus conversion comprises a transgene.

18. The method of claim 7, wherein the method further comprises:
(a) crossing a plant grown from said $F_1$ hybrid soybean seed with itself or a different soybean plant to produce a seed of a progeny plant of a subsequent generation;
(b) growing a progeny plant of a subsequent generation from said seed of a progeny plant of a subsequent generation and crossing the progeny plant of a subsequent generation with itself or a second plant to produce a progeny plant of a further subsequent generation; and
(c) repeating steps (a) and (b) using said progeny plant of a further subsequent generation from step (b) in place of the plant grown from said $F_1$ hybrid soybean seed in step (a), wherein steps (a) and (b) are repeated with sufficient inbreeding to produce an inbred soybean plant derived from the soybean variety A1026138.

19. The method of claim 18, comprising crossing said inbred soybean plant derived from the soybean variety A1026138 with a plant of a different genotype to produce a seed of a hybrid soybean plant derived from the soybean variety A1026138.

20. A method of producing a commodity plant product comprising collecting the commodity plant product from a plant of soybean variety A1026138, wherein a sample of seed of said variety has been deposited under ATCC Accession No. PTA-120935.

21. The method of claim 20, wherein the commodity plant product is protein concentrate, protein isolate, grain, soybean hulls, meal, flour or oil.

22. A soybean commodity plant product produced by the method of claim 20, wherein the commodity plant product comprises at least a first cell of soybean variety A1026138.

* * * * *